(12) United States Patent
Itoh et al.

(10) Patent No.: US 8,329,931 B2
(45) Date of Patent: Dec. 11, 2012

(54) ORGANOALUMINUM COMPOUND

(75) Inventors: Hisanori Itoh, Kanagawa (JP); Yoji Hori, Kanagawa (JP)

(73) Assignee: Takasago International Corporation, Tokyo (JP)

( * ) Notice: Subject to any disclaimer, the term of this patent is extended or adjusted under 35 U.S.C. 154(b) by 29 days.

(21) Appl. No.: 13/115,608

(22) Filed: May 25, 2011

(65) Prior Publication Data
US 2011/0295031 A1 Dec. 1, 2011

(30) Foreign Application Priority Data

May 25, 2010 (JP) .................................. 2010-119457

(51) Int. Cl.
*C07F 5/06* (2006.01)
*C07C 35/08* (2006.01)

(52) U.S. Cl. ........ 556/172; 556/170; 556/175; 556/182; 568/828

(58) Field of Classification Search ................... 556/170, 556/172, 175, 182; 568/828
See application file for complete search history.

(56) References Cited

U.S. PATENT DOCUMENTS

| 6,166,260 | A | 12/2000 | Heise |
| 2002/0133046 | A1 | 9/2002 | Iwata et al. |
| 2008/0167504 | A1 | 7/2008 | Friedrich et al. |
| 2008/0207957 | A1 | 8/2008 | Friedrich et al. |

FOREIGN PATENT DOCUMENTS

| DE | 102005023953 A1 | 11/2006 |
| EP | 2279992 A1 | 2/2011 |
| JP | 59-45661 B2 | 11/1984 |
| JP | 2002-212121 A | 7/2002 |
| JP | 2008-524287 A | 7/2008 |
| JP | 2008-538101 A | 10/2008 |
| JP | 2009-510005 A | 3/2009 |
| JP | 2009510006 A | 3/2009 |
| WO | 2007/039366 A1 | 4/2007 |
| WO | 2007039342 A1 | 4/2007 |
| WO | 2009/144906 A1 | 12/2009 |
| WO | WO 2010071227 A1 | 6/2010 |

OTHER PUBLICATIONS

Communication dated Sep. 26, 2011 from the European Patent Office in counterpart European application No. 11167165.7.
Indo, M. "Synthetic Flavor or Fragrance (Enlarged Edition)", The Chemical Daily Co., Ltd., Mar. 22, 2005, pp. 83-89.
Ishikawa, T. et., al. "Chiral Lewis Acid-Hydroxylamine Hybrid Reagent for Enantioselective Micheal Addition Reaction Directed Towards β-Amino Acids Synthesis", Synlett, Nov. 1998, pp. 1291-1293.
Cativiela, C. et., al. "Asymmetric Synthesis of 2-Aminonorbornane-2-Carboxylic Acids by Diels-Alder Reaction", Tetrahedron: Asymmetry vol. 2, No. 12, 1991, pp. 1295-1304.
Seebach, D. et., al. "Reduction of Ketones with $LiAlH_4$ Complexes of α, α, α$^1$, α$^1$-Tetraaryl-1,3-dioxolane-4,5-dimethanols (TADDOLs): A Combination of Enantioselective Reduction and Clathrate Formation with a Discussion of LAH Reagents Bearing $C_2$-Symmetrical Ligands" Croatica Chemica ACTA, vol. 69, No. 2, 1996, pp. 459-484.
Vinogradov, M. G. et., al. "Organic Chemistry: Asymmetric reduction of ketones with sodium aluminium hydride modified by various chiral diols", Russian Chemical Bulletin, vol. 49, No. 3, Mar. 2000, pp. 460-465.

*Primary Examiner* — Porfirio Nazario Gonzalez
(74) *Attorney, Agent, or Firm* — Sughrue Mion, PLLC

(57) ABSTRACT

A catalyst for obtaining isopulegol of high diastereoselectivity by highly selective cyclization reaction of citronellal is provided. The present invention relates to an organoaluminum compound obtained by reacting at least one organoaluminumoxy compound selected from the group consisting of chain aluminoxanes, cyclic aluminoxanes and bis(dialkylaluminumoxy)alkylboranes, with at least one hydroxy compound selected from the group consisting of diarylphenols, bis(diarylphenol) compounds, biaryldiols, dimethanols and silanols.

3 Claims, 4 Drawing Sheets

ORGANOALUMINUM COMPOUND

CROSS-REFERENCE TO RELATED APPLICATIONS

This application claims priority from Japanese Patent Application No. 2010-119457 filed on May 25, 2010, the entire subject matter of which is incorporated herein by reference.

BACKGROUND OF THE INVENTION

1. Technical Field of the Invention

The present invention relates to an organoaluminum compound obtained by reacting an organoaluminumoxy compound with hydroxy compound. The present invention further relates to use of the organoaluminum compound as a catalyst. The present invention further relates to a method for producing isopulegol by cyclizing citronellal using the organoaluminum compound as a catalyst.

2. Background of the Invention

Conventionally, menthol, particularly, l-menthol, is very important as flavor or fragrance having fresh-feeling and its use is very wide. As the synthesis method of menthol, a method of obtaining dl-menthol by optical resolution and a method of obtaining menthol by an asymmetric synthesis method are known (Non-Patent Document 1). In the production step of l-menthol by the asymmetric synthesis method, l-menthol is obtained by hydrogenating l-isopulegol which is a precursor. However, in order to synthesize the l-isopulegol, selective cyclization reaction of d-citronellal is an important step.

As the selective cyclization reaction of d-citronellal, the disclosed method, that is, the production of l-isopulegol using zinc bromide as a catalyst, was already performed (Patent Document 1). In this case, the ratio between l-isopulegol and other isomers is about 90% as diastereoselectivity.

Selective cyclization reaction by an aluminum siloxide catalyst is reported (Patent Documents 2 and 3). In this case, the diastereoselectivity is up to 96%.

Selective cyclization reactions by tris(2,6-diarylphenoxy) aluminum and its similar catalyst are reported (Patent Documents 4 to 8). In those Patent Documents, the diastereoselectivity of isopulegol formed is about 96%.

On the other hand, regarding an aluminum catalyst having a diol skeleton which is a ligand derived from tartaric acid, there are many reports (Patent Document 9) (Non-Patent Documents 2 to 5). However, those reports each are concerned with only an aluminum catalyst having a cationic complex or a specific substituent such as halogen group and aminohydroxy group.

Patent Documents

Patent Document 1: JP-B-59-45661
Patent Document 2: JP-T-2009-510005 (the term "JP-T" used herein means a published Japanese translation of a PCT patent application)
Patent Document 3: JP-T-2009-510006
Patent Document 4: JP-A-2002-212121
Patent Document 5: JP-T-2008-524287
Patent Document 6: JP-T-2008-538101
Patent Document 7: DE-A-102005023953
Patent Document 8: WO2009/144906
Patent Document 9: U.S. Pat. No. 6,166,260

Non-Patent Document

Non-Patent Document 1: Synthetic Flavor or Fragrance (Enlarged edition), Motoichi Indo, The Chemical Daily Co., Ltd., pp. 83-89, published Mar. 22, 2005
Non-Patent Document 2: Synlett, 1998, pp. 1291-1293
Non-Patent Document 3: Tetrahedron: Asymmetry, 1991, Vol. 2, No. 12, pp. 1295-1304
Non-Patent Document 4: CROATIA CHEMICA ACTA, 1996, 69, pp. 459-484
Non-Patent Document 5: Russian Chemical Bulletin, 2000, 49, pp. 460-465

SUMMARY OF THE INVENTION

However, in the methods of Patent Documents 1 and 2, the diastereoselectivity of isopulegol is not so satisfactory.

In the catalysts of Patent Documents 3 to 5, the diastereoselectivity of isopulegol formed is 96% or more. However, the organoaluminum, compound used as a precursor of the catalyst uses a compound instable to moisture and air, such as trialkylaluminum, and care should be taken to catalyst preparation.

The present invention relates to a catalyst for obtaining isopulegol of high diastereoselectivity by high selective cyclization reaction of citronellal. In addition, the present invention relates to a method for producing l-isopulegol which is an important synthesis precursor of l-menthol and is useful as a material of flavor or fragrance, particularly obtained by high selective cyclization reaction of d-citronellal using the catalyst.

As a result of intensive investigations to solve the above problems, the present inventors have succeeded to obtain an organoaluminum compound, which has hitherto not been reported, by reacting a relatively stable organoaluminum compound with various hydroxy compounds.

They have further found that citronellal is cyclized by using the organoaluminum compound as a catalyst, and isopulegol in four kinds of isomers of isopulegol, isoisopulegol, neoisopulegol and neoisoisopulegol is obtained with high selectivity of 96% or more in terms of isomer ratio with high yield, and have reached to complete the present invention.

The present invention provides the following organoaluminum compound and method for producing isopulegol.

1. An organoaluminum compound obtained by reacting at least one organoaluminumoxy compound selected from the group consisting of chain aluminoxanes represented by the following general formula (1), cyclic aluminoxanes represented by the following general formula (2) and bis(dialkylaluminumoxy)alkylboranes represented by the following general formula (3), with at least one hydroxy compound selected from the group consisting of diarylphenols represented by the following general formula (4), bis(diarylphenol) compounds represented by the following general formula (5), biaryldiols represented by the following general formula (6), dimethanols represented by the following general formula (7) and silanols represented by the following general formula (8):

[Chem. 1]

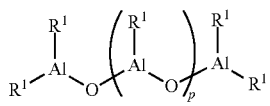
(1)

wherein $R^1$ represents an alkyl group having from 1 to 6 carbon atoms, an alicyclic group having from 5 to 8 carbon atoms, or an aralkyl group having from 7 to 12 carbon atoms, which may have a substituent, and the plural $R^1$ may be the same or different; and p is an integer of from 0 to 40;

[Chem. 2]

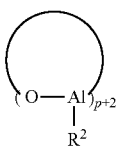
(2)

wherein $R^2$ represents an alkyl group having from 1 to 6 carbon atoms, an alicyclic group having from 5 to 8 carbon atoms, or an aralkyl group having from 7 to 12 carbon atoms, which may have a substituent; and p is an integer of from 0 to 40;

[Chem. 3]

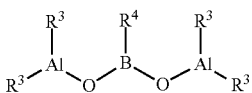
(3)

wherein $R^3$ represents an alkyl group having from 1 to 6 carbon atoms, an alicyclic group having from 5 to 8 carbon atoms, or an aralkyl group having from 7 to 12 carbon atoms, which may have a substituent, and the plural $R^3$ may be the same or different; and $R^4$ represents an alkyl group having from 1 to 6 carbon atoms, an alicyclic group having from 5 to 8 carbon atoms, or an aralkyl group having from 7 to 12 carbon atoms, which may have a substituent;

[Chem. 4]

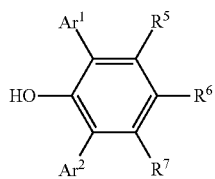
(4)

wherein $Ar^1$ and $Ar^2$ each independently represent an aryl group having from 6 to 15 carbon atoms, which may have a substituent, or a heteroaryl group having from 2 to 15 carbon atoms, which may have a substituent; $R^5$, $R^6$ and $R^7$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; and $R^5$ and $R^6$, or $R^6$ and $R^7$ may be combined with each other to form a condensed benzene ring, a condensed substituted-benzene ring, trimethylene group, tetramethylene group, pentamethylene group, methylenedioxy group, ethylenedioxy group or trimethylenedioxy group;

[Chem. 5]

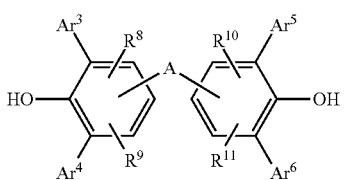
(5)

wherein $Ar^3$, $Ar^4$, $Ar^5$ and $Ar^6$ each independently represent an aryl group having from 6 to 15 carbon atoms, which may have a substituent, or a heteroaryl group having from 2 to 15 carbon atoms, which may have a substituent; $R^8$, $R^9$, $R^{10}$ and $R^{11}$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; $R^8$ and $R^9$, and/or $R^{10}$ and $R^{11}$ may be combined with each other to form a condensed benzene ring, a condensed substituted-benzene ring, trimethylene group, tetramethylene group, pentamethylene group, methylenedioxy group, ethylenedioxy group or trimethylenedioxy group; and $R^8$ or $R^9$ and/or $R^{10}$ or $R^{11}$ may be combined with A to form a cyclic aromatic ring or a non-aromatic ring; and A is (1) a single bond, (2) a linear or branched and/or cyclic hydrocarbon group having from 1 to 25 carbon atoms, which may have a substituent and/or an unsaturated bond, (3) an arylene group having from 6 to 15 carbon atoms, which may have a substituent, (4) a heteroarylene group having from 2 to 15 carbon atoms, which may have a substituent, (5) a functional group or a hetero element, which is selected from the group consisting of —O—, —S—, —N($R^{12}$)—, —S(O)—, —C(O)—, —S(O)$_2$—, —P($R^{12}$)—, —($R^{12}$)P(O)— and —Si($R^{13}R^{14}$)—, wherein $R^{12}$ to $R^{14}$ each independently represent an alkyl group having from 1 to 6 carbon atoms, an alicyclic group having from 5 to 8 carbon atoms, an aralkyl group having from 7 to 12 carbon atoms, which may have a substituent, or an aryl group having from 6 to 10 carbon atoms, which may have a substituent;

[Chem. 6]

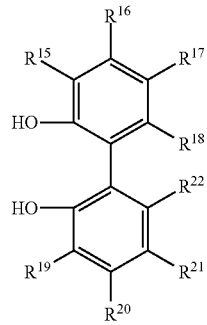

(6)

wherein $R^{15}$, $R^{16}$, $R^{17}$, $R^{18}$, $R^{19}$, $R^{20}$, $R^{21}$ and $R^{22}$ each independently represent hydrogen atom, an alkyl group having from 1 to 8 carbon atoms, a perfluoroalkyl group having from 1 to 4 carbon atoms, an alkoxy group having from 1 to 8 carbon atoms, an alicyclic group having from 5 to 8 carbon atoms, an aralkyl group having from 7 to 12 carbon atoms, which may have a substituent, a halogen atom, an organosilyl group, an aryl group having from 6 to 15 carbon atoms, which may has a substituent, a dialkylamino group having from 2 to 8 carbon atoms, a thioalkoxy group having from 1 to 4 carbon atoms, a nitro group or a polymer chain, and at least one pair of $R^{15}$ and $R^{16}$, $R^{16}$ and $R^{17}$, $R^{17}$ and $R^{18}$, $R^{15}$ and $R^{22}$, $R^{19}$ and $R^{20}$, $R^{20}$ and $R^{21}$, and $R^{21}$ and $R^{22}$ may be combined with each other to form a condensed benzene ring, a condensed substituted-benzene ring, trimethylene group, tetramethylene group, pentamethylene group, methylenedioxy group, ethylenedioxy group or trimethylenedioxy group;

[Chem. 7]

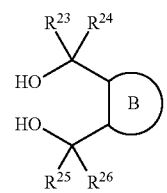

(7)

wherein $R^{23}$, $R^{24}$, $R^{25}$ and $R^{26}$ each independently represent hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may has a substituent, a heteroaryl group having from 2 to 15 carbon atoms, which may have a substituent, a dialkylamino group having from 2 to 8 carbon atoms, a thioalkoxy group having from 1 to 4 carbon atoms, a nitro group or a polymer chain; $R^{23}$ and $R^{24}$, and/or $R^{25}$ and $R^{26}$ may be combined with each other to form a 3- to 9-membered ring which may have a hetero element; and the ring B is a 3- to 8-membered ring which may have a hetero element; and

[Chem. 8]

(8)

wherein $R^{27}$, $R^{28}$ and $R^{29}$ each independently represent an alkyl group having from 1 to 10 carbon atoms, an alicyclic group having from 5 to 8 carbon atoms, an aralkyl group having from 7 to 12 carbon atoms, an aryl group having from 6 to 10 carbon atoms, which may have a substituent, a heteroaryl group having from 2 to 15 carbon atoms, which may have a substituent or a polymer chain.

2. A method for producing isopulegol represented by the following formula (10), comprising selectively cyclizing citronellal represented by the following formula (9) using the organoaluminum compound according to the above 1 as a catalyst;

[Chem. 9]

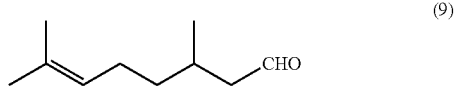

(9)

[Chem. 10]

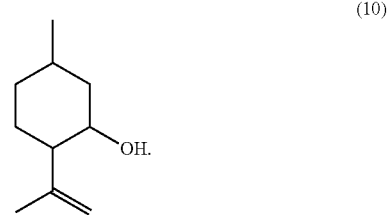

(10)

3. A method for producing optically active isopulegol represented by the following formula (12), comprising selectively cyclizing citronellal represented by the following formula (11) using the organoaluminum compound according to the above 1 as a catalyst;

[Chem. 11]

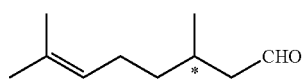

(11)

wherein * means an asymmetric carbon atom

[Chem. 12]

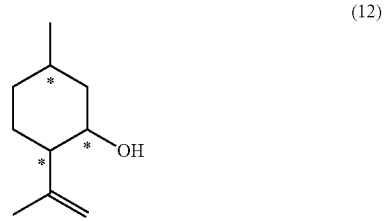

(12)

wherein * means an asymmetric carbon atom.

As described above, the present invention provides an organoaluminum compound obtained by reacting relatively stable organoaluminumoxy compound with various hydroxyl compounds. Use of the organoaluminum compound as a catalyst can give high diastereoselectivity in a selective cyclization reaction of citronellal. Furthermore, by filtering a reaction solution, the catalyst can be reutilized, which is industrially advantageous. The ligand after catalyst deactivation is recovered, and can again be reutilized as the catalyst.

The present invention can further provide a method for producing isopulegol which is useful as a material of flavor or fragrance and is an important synthesis precursor of menthol, by using the organoaluminum compound as a catalyst with high yield and high selectivity.

DETAILED DESCRIPTION OF THE INVENTION

Figure 1:
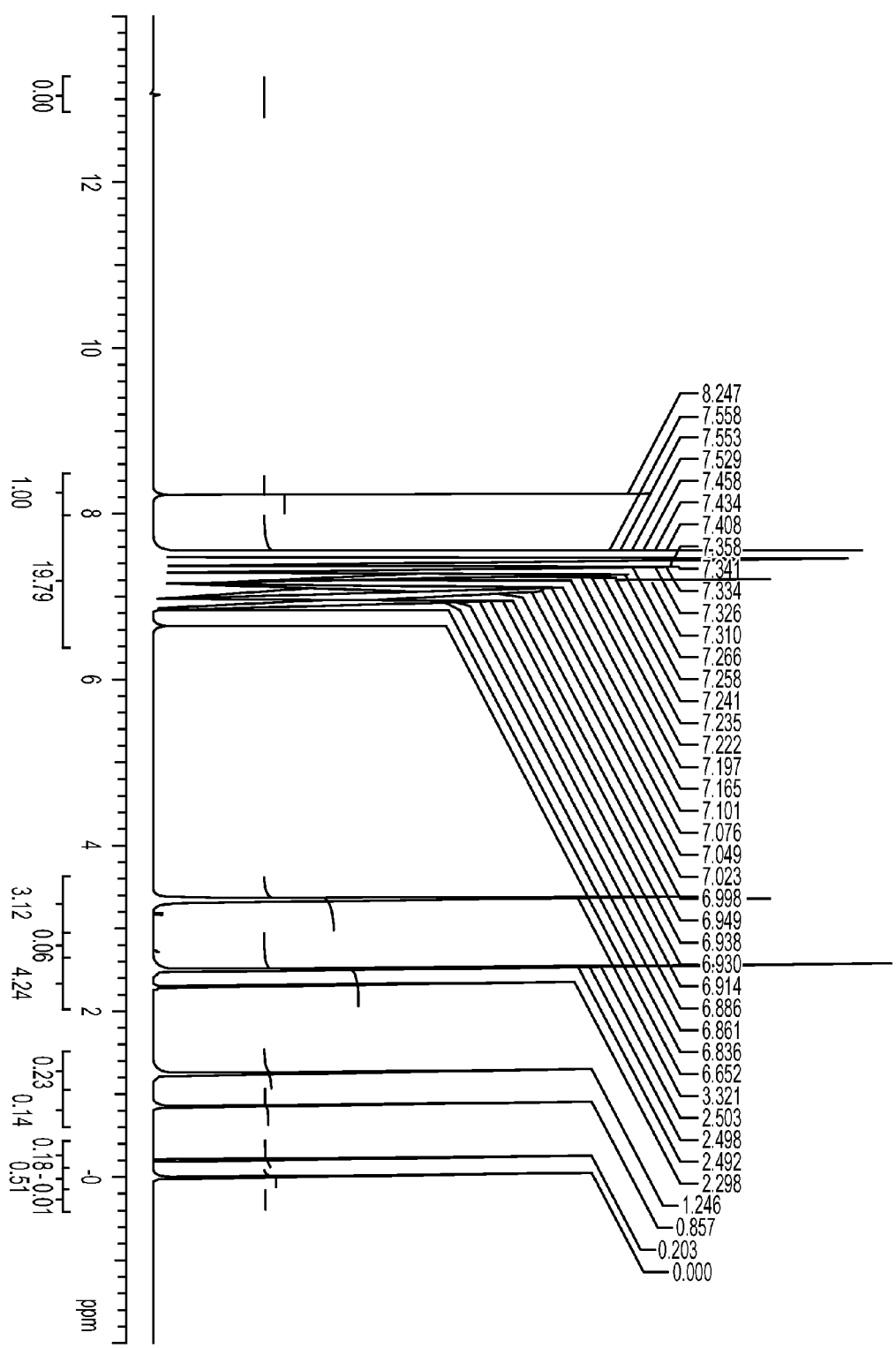
FIG. 1 is a view showing NMR spectrum of 2,6-diphenylphenol and methylaluminoxane.

The present invention is described in detail below.

Organoaluminumoxy compound used to produce the organoaluminum compound of the present invention is at least one organoaluminumoxy compound selected from the group consisting of chain aluminoxanes represented by the following general formula (1), cyclic aluminoxanes represented by the following general formula (2) and bis(dialkylaluminumoxy)alkylboranes represented by the following general formula (3).

[Chem. 13]

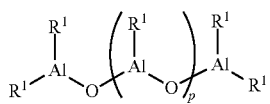

(1)

In the general formula (1), $R^1$ represents an alkyl group having from 1 to 6 carbon atoms, an alicyclic group having from 5 to 8 carbon atoms, or an aralkyl group having from 7 to 12 carbon atoms, which may have a substituent, and the plural $R^1$ may be the same or different; and p is an integer of from 0 to 40.

[Chem. 14]

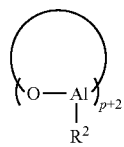

(2)

In the general formula (2), $R^2$ represents an alkyl group having from 1 to 6 carbon atoms, an alicyclic group having from 5 to 8 carbon atoms, or an aralkyl group having from 7 to 12 carbon atoms, which may have a substituent; and p is an integer of from 0 to 40.

[Chem. 15]

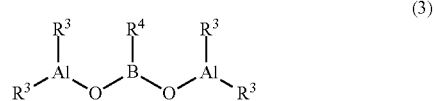

(3)

In the general formula (3), $R^3$ represents an alkyl group having from 1 to 6 carbon atoms, an alicyclic group having from 5 to 8 carbon atoms, or an aralkyl group having from 7 to 12 carbon atoms, which may have a substituent, and the plural $R^3$ may be the same or different; and $R^4$ represents an alkyl group having from 1 to 6 carbon atoms, an alicyclic group having from 5 to 8 carbon atoms, or an aralkyl group having from 7 to 12 carbon atoms, which may have a substituent.

In the chain aluminoxanes represented by the general formula (1), $R^1$ represents an alkyl group having from 1 to 6 carbon atoms, an alicyclic group having from 5 to 8 carbon atoms, or an aralkyl group having from 7 to 12 carbon atoms, which may have a substituent, and the plural $R^1$ may be the same or different; and p is an integer of from 0 to 40.

In the cyclic aluminoxanes represented by the general formula (2), $R^2$ represents an alkyl group having from 1 to 6 carbon atoms, an alicyclic group having from 5 to 8 carbon atoms, or an aralkyl group having from 7 to 12 carbon atoms, which may have a substituent; and p is an integer of from 0 to 40.

In the bis(dialkylaluminumoxy)alkylboranes represented by the general formula (3), $R^3$ represents an alkyl group having from 1 to 6 carbon atoms, an alicyclic group having from 5 to 8 carbon atoms, or an aralkyl group having from 7 to 12 carbon atoms, which may have a substituent, and the plural $R^3$ may be the same or different; and $R^4$ represents an alkyl group having from 1 to 6 carbon atoms, an alicyclic group having from 5 to 8 carbon atoms, or an aralkyl group having from 7 to 12 carbon atoms, which may have a substituent.

The specific substituents in the organoaluminumoxy compounds represented by the general formulae (1) to (3) include the following groups.

Examples of the alkyl group having from 1 to 6 carbon atoms include methyl group, ethyl group, n-propyl group, isopropyl group, n-butyl group, isobutyl group, sec-butyl group, tert-butyl group, pentyl group and hexyl group.

Examples of the alicyclic group having from 5 to 8 carbon atoms include cyclopentyl group, cyclohexyl group, methylcyclohexyl group, cycloheptyl group and cyclooctyl group.

Examples of the aralkyl group having from 7 to 12 carbon atoms, which may have a substituent include benzyl group, 1-phenylethyl group, 2-phenylethyl group, α-naphthylmethyl group and β-naphthylmethyl group.

Examples of the substituent include an alkyl group having from 1 to 6 carbon atoms such as methyl group, ethyl group, n-propyl group, isopropyl group, n-butyl group, isobutyl group, sec-butyl group, tert-butyl group, pentyl group and hexyl group; an alicyclic group having from 5 to 8 carbon atoms such as cyclopentyl group, cyclohexyl group and cycloheptyl group; a perfluoroalkyl group having from 1 to 4 carbon atoms such as trifluoromethyl group, pentafluoroethyl group, heptafluoropropyl group and nonafluorobutyl group;

an alkoxy group having from 1 to 4 carbon atoms such as methoxy group, ethoxy group, n-propoxyl group, isopropoxy group, n-butoxy group, isobutoxy group, sec-butoxy group and tert-butoxy group; a halogen atom such as fluorine atom, chlorine atom, bromine atom and iodine atom; an aralkyl group having from 7 to 12 carbon atoms such as benzyl group, phenylethyl group and naphthylmethyl group; a tri-($C_{1-6}$) alkylsilyl group such as trimethylsilyl group, triethylsilyl group, triisopropylsilyl group, dimethylisopropylsilyl group, diethylisopropylsilyl group, dimethyl(2,3-dimethyl-2-butyl) silyl group, tert-butyldimethylsilyl group and dimethylhexylsilyl group; and a dialkylamino group having from 2 to 8 carbon atoms such as dimethylamino group, diethylamino group and dibutylamino group.

In addition, p is an integer of from 0 to 40, and preferably from 2 to 30.

The organoaluminumoxy compound represented by the general formulae (1) and (2) is a compound called as aluminoxane. Of the aluminoxane, methylaluminoxane, ethylaluminoxane, isobutylaluminoxane and methylisobutylaluminoxane are preferred, and methylaluminoxane is particularly preferred. The aluminoxane can be co-used with several kinds in each group and among each group. The aluminoxane can be prepared under the conventional various conditions.

The organoaluminumoxy compound represented by the general formula (3) can be obtained by the reaction of one kind of trialkylaluminum represented by $(R^3)_3Al$ or two kinds or more of the trialkylaluminum, and alkylboronic acid represented by the general formula $R^4B(OH)_2$, in a molar ratio of from 10:1 to 1:1.

The hydroxy compound used to produce the organoaluminum compound of the present invention is at least one hydroxy compound selected from the group consisting of diarylphenols represented by the following general formula (4), bis(diarylphenol) compounds represented by the following general formula (5), biaryldiols represented by the following formula (6), dimethanols represented by the following general formula (7) and silanols represented by the following general formula (8).

[Chem. 16]

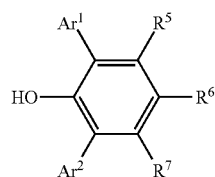

(4)

In the general formula (4), $Ar^1$ and $Ar^2$ each independently represent an aryl group having from 6 to 15 carbon atoms, which may have a substituent, and a heteroaryl group having from 2 to 15 carbon atoms, which may have a substituent; $R^5$, $R^6$ and $R^7$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; and $R^5$ and $R^6$, or $R^6$ and $R^7$ may be combined with each other to form a condensed benzene ring, a condensed substituted-benzene ring, trimethylene group, tetramethylene group, pentamethylene group, methylenedioxy group, ethylenedioxy group or trimethylenedioxy group.

[Chem. 17]

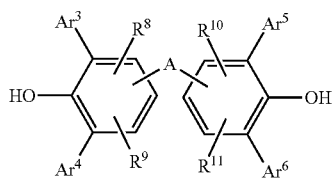

(5)

In the general formula (5), $Ar^3$, $Ar^4$, $Ar^5$ and $Ar^6$ each independently represent an aryl group having from 6 to 15 carbon atoms, which may have a substituent, or a heteroaryl group having from 2 to 15 carbon atoms, which may have a substituent; $R^8$, $R^9$, $R^{10}$ and $R^{11}$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; $R^8$ and $R^9$, and/or $R^{10}$ and $R^{11}$ may be combined with each other to form a condensed benzene ring, a condensed substituted-benzene ring, trimethylene group, tetramethylene group, pentamethylene group, methylenedioxy group, ethylenedioxy group or trimethylenedioxy group; and $R^8$ or $R^9$ and/or $R^{10}$ or $R^{11}$ may be combined with A to form a cyclic aromatic ring or a non-aromatic ring; and A is (1) a single bond, (2) a linear or branched and/or cyclic hydrocarbon group having from 1 to 25 carbon atoms, which may have a substituent and/or an unsaturated bond, (3) an arylene group having from 6 to 15 carbon atoms, which may have a substituent, (4) a heteroarylene group having from 2 to 15 carbon atoms, which may have a substituent, (5) a functional group or a hetero element, selected from the group consisting of —O—, —S—, —N($R^{12}$)—, —S(O)—, —C(O)—, —S(O)$_2$—, —P($R^{12}$)—, —($R^{12}$)P(O)— and —Si($R^{13}R^{14}$)—, wherein $R^{12}$ to $R^{14}$ each independently represent an alkyl group having from 1 to 6 carbon atoms, an alicyclic group having from 5 to 8 carbon atoms, an aralkyl group having from 7 to 12 carbon atoms, which may have a substituent, or an aryl group having from 6 to 10 carbon atoms, which may have a substituent.

[Chem. 18]

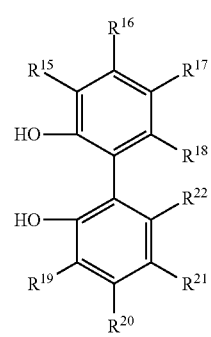

(6)

In the general formula (6), $R^{15}$, $R^{16}$, $R^{17}$, $R^{18}$, $R^{19}$, $R^{20}$, $R^{21}$ and $R^{22}$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may has a substituent, a dialkylamino group having from 2 to 8 carbon atoms, a thioalkoxy group having from 1 to 4 carbon atoms, a nitro group or a polymer chain, and at least one pair of $R^{15}$ and $R^{16}$, $R^{16}$ and $R^{17}$, $R^{17}$ and $R^{18}$, $R^{15}$ and $R^{22}$, $R^{19}$ and $R^{20}$, $R^{20}$ and $R^{21}$, and $R^{21}$ and $R^{22}$ may be combined with each other to form a condensed benzene ring, a condensed substituted-benzene ring, trimethylene group, tetramethylene group, pentamethylene group, methylenedioxy group, ethylenedioxy group or trimethylenedioxy group.

[Chem. 19]

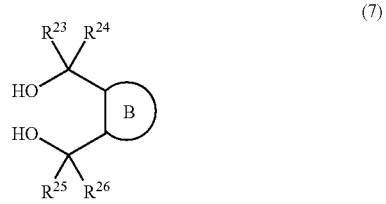

(7)

In the general formula (7), $R^{23}$, $R^{24}$, $R^{25}$ and $R^{26}$ each independently represent hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may has a substituent, a heteroaryl group having from 2 to 15 carbon atoms, which may have a substituent, a dialkylamino group having from 2 to 8 carbon atoms, a thioalkoxy group having from 1 to 4 carbon atoms, a nitro group or a polymer chain; $R^{23}$ and $R^{24}$, and/or $R^{25}$ and $R^{26}$ may be combined with each other to form a 3- to 9-membered ring which may have a hetero element; and the ring B is a 3- to 8-membered ring which may have a hetero element.

[Chem. 20]

(8)

In the general formula (8), $R^{27}$, $R^{28}$ and $R^{29}$ each independently represent an alkyl group having from 1 to 10 carbon atoms, an alicyclic group having from 5 to 8 carbon atoms, an aralkyl group having from 7 to 12 carbon atoms, which may have a substituent, an aryl group having from 6 to 15 carbon atoms, which may has a substituent, a heteroaryl group having from 2 to 15 carbon atoms, which may have a substituent or a polymer chain.

In the diarylphenols represented by the general formula (4), $Ar^1$ and $Ar^2$ each independently represent an aryl group having from 6 to 15 carbon atoms, which may have a substituent, or a heteroaryl group having from 2 to 15 carbon atoms, which may have a substituent; $R^5$, $R^6$ and $R^7$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group, a thioalkoxy group, a nitro group or a polymer chain; and $R^5$ and $R^6$, or $R^6$ and $R^7$ may be combined with each other to form a ring.

In the bis(diarylphenyl) compounds represented by the general formula (5), $Ar^3$, $Ar^4$, $Ar^5$ and $Ar^6$ each independently represent an aryl group having from 6 to 15 carbon atoms, which may have a substituent, or a heteroaryl group having from 2 to 15 carbon atoms, which may have a substituent; $R^8$, $R^9$, $R^{10}$ and $R^{11}$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; $R^8$ and $R^9$, and/or $R^{10}$ and $R^{11}$ may be combined with each other to form a condensed benzene ring, a condensed substituted-benzene ring, trimethylene group, tetramethylene group, pentamethylene group, methylenedioxy group, ethylenedioxy group or trimethylenedioxy group; $R^8$ or $R^9$ and/or $R^{10}$ or $R^{11}$ may be combined with A to form a cyclic aromatic ring or a non-aromatic ring; and A is (1) a single bond, (2) a linear or branched and/or cyclic hydrocarbon group having from 1 to 25 carbon atoms, which may have a substituent and/or an unsaturated bond, (3) an arylene group having from 6 to 15 carbon atoms, which may have a substituent, (4) a heteroarylene group having from 2 to 15 carbon atoms, which may have a substituent, (5) a functional group or a hetero element selected from the group consisting of —O—, —S—, —N($R^{12}$)—, —S(O)—, —C(O)—, —S(O)$_2$—, —P($R^{12}$)—, —($R^{12}$)P(O)— and —Si($R^{13}R^{14}$)—, wherein $R^{12}$ to $R^{14}$ each independently represent an alkyl group having from 1 to 6 carbon atoms, an alicyclic group having from 5 to 8 carbon atoms, an aralkyl group having from 7 to 12 carbon atoms, which may have a substituent, or an aryl group having from 6 to 10 carbon atoms, which may have a substituent.

In the biaryldiols represented by the general formula (6), $R^{15}$, $R^{16}$, $R^{17}$, $R^{18}$, $R^{19}$, $R^{20}$, $R^{21}$ and $R^{22}$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may has a substituent, a dialkylamino group having from 2 to 8 carbon atoms, a thioalkoxy group having from 1 to 4 carbon atoms, a nitro group or a polymer chain; and at least one pair of $R^{15}$ and $R^{16}$, $R^{16}$ and $R^{17}$, $R^{17}$ and $R^{18}$, $R^{15}$ and $R^{22}$, $R^{19}$ and $R^{20}$, $R^{20}$ and $R^{21}$, and $R^{21}$ and $R^{22}$ may be combined with each other to form a condensed benzene ring, a condensed substituted-benzene ring, trimethylene group, tetramethylene group, pentamethylene group, methylenedioxy group, ethylenedioxy group or trimethylenedioxy group.

In the dimethanols represented by the general formula (7), $R^{23}$, $R^{24}$, $R^{25}$ and $R^{26}$ each independently represent hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may has a substituent, a heteroaryl group having from 2 to 15 carbon atoms, which may have a substituent, a dialkylamino group having from 2 to 8 carbon atoms, a thioalkoxy group having from 1 to 4 carbon atoms, a nitro group or a polymer chain; $R^{23}$ and $R^{24}$, and/or $R^{25}$ and $R^{26}$ may be combined with each other to form a 3- to 9-membered ring which may have a heteroelement; and the ring B is a 3- to 8-membered ring which may have a hetero element.

In the silanols represented by the general formula (8), $R^{27}$, $R^{28}$ and $R^{29}$ each independently represent an alkyl group having from 1 to 10 carbon atoms, an alicyclic group having from 5 to 8 carbon atoms, an aralkyl group having from 7 to 12 carbon atoms, which may have a substituent, an aryl group having from 6 to 15 carbon atoms, which may has a substituent, a heteroaryl group having from 2 to 15 carbon atoms, which may have a substituent or a polymer chain.

The specific substituents in the hydroxy compounds represented by the general formulae (4) to (8) include the following groups.

Examples of the aryl group having from 6 to 15 carbon atoms, which may have a substituent include benzyl group, α-naphthyl group and β-naphthyl group.

Examples of the substituent include an alkyl group having from 1 to 6 carbon atoms such as methyl group, ethyl group, n-propyl group, isopropyl group, n-butyl group, isobutyl group, sec-butyl group, tort-butyl group, pentyl group and hexyl group; an alicyclic group having from 5 to 8 carbon atoms such as cyclopentyl group, cyclohexyl group and cycloheptyl group; a perfluoroalkyl group having from 1 to 4 carbon atoms such as trifluoromethyl group, pentafluoroethyl group, heptafluoropropyl group and nonafluorobutyl group; an alkoxy group having from 1 to 4 carbon atoms such as methoxy group, ethoxy group, n-propoxyl group, isopropoxy group, n-butoxy group, isobutoxy group, sec-butoxy group and tert-butoxy group; a halogen atom such as fluorine atom, chlorine atom, bromine atom and iodine atom; an aralkyl group having from 7 to 12 carbon atoms such as benzyl group, phenylethyl group and naphthylmethyl group; a tri-($C_{1-6}$) alkylsilyl group such as trimethylsilyl group, triethylsilyl group, triisopropylsilyl group, dimethylisopropylsilyl group, diethylisopropylsilyl group, dimethyl(2,3-dimethyl-2-butyl)silyl group, tert-butyldimethylsilyl group and dimethylhexylsilyl group; and a dialkylamino group having from 2 to 8 carbon atoms such as dimethylamino group, diethylamino group and dibutylamino group. Further examples include polymer chains such as 6,6-nylon chain, vinyl polymer chain and styrene polymer chain.

Examples of the heteroaryl group having from 2 to 15 carbon atoms, which may have a substituent, include furyl group, thienyl group, pyronyl group, benzofuryl group, isobenzofuryl group, benzothienyl group, indolyl group, isoindolyl group, carbazoyl group, pyridyl group, quinolyl group, isoquinolyl group, pyrazyl group and ferrocenyl group. Examples of the substituent include the same substituents as exemplified in the aryl group.

Examples of the alkyl group having from 1 to 8 carbon atoms include methyl group, ethyl group, n-propyl group, isopropyl group, n-butyl group, isobutyl group, sec-butyl group, tert-butyl group, pentyl group, hexyl group, heptyl group and octyl group.

Examples of the alicyclic group having from 5 to 8 carbon atoms include cyclopentyl group, cyclohexyl group, methylcyclohexyl group, cycloheptyl group and cyclooctyl group.

Examples of the perfluoroalkyl group having from 1 to 4 carbon atoms include trifluoromethyl group, pentafluoroethyl group, heptafluoropropyl group and nonafluorobutyl group.

Examples of the alkoxy group having from 1 to 8 carbon atoms include methoxy group, ethoxy group, n-propoxy group, isopropoxy group, n-butoxy group, isobutoxy group, sec-butoxy group, tert-butoxy group, pentoxy group, hexoxy group, heptoxy group and octoxy group.

Examples of the aralkyl group having from 7 to 12 carbon atoms, which may have a substituent, include benzyl group, 1-phenylethyl group, 2-phenylethyl group, α-naphthylmethyl group and β-naphthylmethyl group. Examples of the substituents include the same substituents as exemplified in the aryl group.

Examples of the halogen atom include fluorine atom, chlorine atom, bromine atom and iodine atom.

Example of the organosilyl group includes tri-substituted silyl group. The substituents are three substituents selected from an alkyl group having from 1 to 6 carbon atoms, an aryl group having from 6 to 18 carbon atoms and an aralkylsilyl group having from 7 to 19 carbon atoms, and those may be the same or different. Examples of the alkyl group having from 1 to 6 carbon atoms include methyl group, ethyl group, isopropyl group, 2,3-dimethyl-2-butyl group, hexyl group and tert-butyl group. Examples of the aryl group having from 6 to 18 carbon atoms include phenyl group and naphthyl group. Examples of the aralkyl group having from 7 to 19 carbon atoms include benzyl group and p-xylyl group.

Examples of the organosilyl include tri-substituted silyl groups, for example, tri-$C_{1-6}$ alkylsilyl groups such as trimethylsilyl group, triethylsilyl group, triisopropylsilyl group, dimethylisopropylsilyl group, diethylisopropylsilyl group, dimethyl(2,3-dimethyl-2-butyl)silyl group, tert-butyldimethylsilyl group and dimethylhexylsilyl group; di-$C_{1-6}$ alkyl-$C_{6-18}$ arylsilyl groups such as dimethylcumylsilyl group; di-$C_{6-18}$ aryl-$C_{1-6}$ alkylsilyl groups such as tert-butyldiphenylsilyl group and diphenylmethylsilyl group; tri-$C_{6-18}$ arylsilyl groups such as triphenylsilyl group; and tri-$C_{7-19}$ aralkylsilyl group such as tribenzylsilyl group and tri-p-xylylsilyl group.

Examples of the dialkylamino group having from 2 to 8 carbon atoms include dimethylamino group, diethylamine group, dipropylamino group, diisopropylamino group and dibutylamino group.

Examples of the thioalkyl group having from 1 to 4 carbon atoms include methylthio group, ethylthio group, n-propylthio group, isopropylthio group, n-butylthio group, isobutylthio group, sec-butylthio group and tert-butylthio group.

Examples of the polymer chain include 6,6-nylon chain, vinyl polymer chain and styrene polymer chain.

In the general formula (4), $R^5$ and $R^6$, or $R^6$ and $R^7$ may be combined with each other to form a condensed benzene ring, a condensed substituted-benzene ring, trimethylene group, tetramethylene group, pentamethylene group, methylenedioxy group, ethylenedioxy group or trimethylenedioxy group.

In the general formula (5), $R^8$ and $R^9$, and/or $R^{10}$ and $R^{11}$ may be combined with each other to form a condensed benzene ring, a condensed substituted-benzene ring, trimethylene group, tetramethylene group, pentamethylene group, methylenedioxy group, ethylenedioxy group or trimethylenedioxy group.

In the general formula (6), at least one pair of $R^{15}$ and $R^{16}$, $R^{16}$ and $R^{17}$, $R^{17}$ and $R^{18}$, $R^{15}$ and $R^{22}$, $R^{19}$ and $R^{20}$, $R^{20}$ and $R^{21}$, and $R^{21}$ and $R^{22}$ may be combined with each other to form a condensed benzene ring, a condensed substituted-benzene ring, trimethylene group, tetramethylene group, pentamethylene group, methylenedioxy group, ethylenedioxy group or trimethylenedioxy group.

The condensed benzene ring, condensed substituted-benzene ring, trimethylene group, tetramethylene group, pentamethylene group, methylenedioxy group, ethylenedioxy group or trimethylenedioxy group may have an inert functional group as the substituent, and may preferably have from 0 to 4 substituents. Examples of the substituent include the same substituents as exemplified in the aryl group.

At least one selected from the hydroxy compounds represented by the general formulae (4), (5) and (6) may form a polymer through the substituent or carbon chain present in the condensed benzene ring, condensed substituted-benzene ring, trimethylene group, tetramethylene group, pentamethylene group, methylenedioxy group, ethylenedioxy group or trimethylenedioxy group.

In the general formula (5), $R^8$ or $R^9$ and/or $R^{10}$ or $R^{11}$ may be combined with A to form a cyclic aromatic ring or a non-aromatic ring. In this case, the bis(diarylphenol) compounds represented by the general formula (5) used in the present invention have, for example, a tricyclic basic structure such as an anthracene basic structure having the following general formula (5a) or the basic structure of the following general formula (5b).

[Chem. 21]

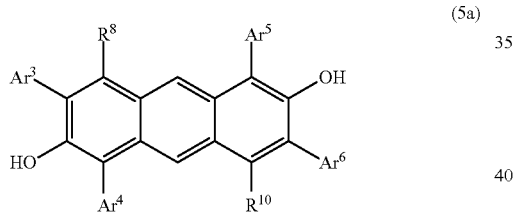

(5a)

[Chem. 22]

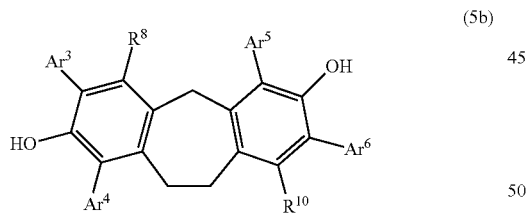

(5b)

The general formula (5a) and the general formula (5b) may be a tricyclic basic structure having a hetero element in the basic structure.

In the general formula (5), A is (1) a single bond, (2) a linear or branched and/or cyclic hydrocarbon group having from 1 to 25 carbon atoms, which may have a substituent and/or an unsaturated bond, (3) an arylene group having from 6 to 15 carbon atoms, which may have a substituent, (4) a heteroarylene group having from 2 to 15 carbon atoms, which may have a substituent, or (5) a functional group or a hetero element selected from the group consisting of —O—, —S—, —N($R^{12}$)—, —S(O)—, —C(O)—, —S(O)$_2$—, —P($R^{12}$)—, —($R^{12}$)P(O)— and —Si($R^{13}R^{14}$)—, wherein $R^{12}$ to $R^{14}$ each independently represent an alkyl group having from 1 to 6 carbon atoms, an alicyclic group having from 5 to 8 carbon atoms, an aralkyl group having from 7 to 12 carbon atoms, which may have a substituent, or an aryl group having from 6 to 10 carbon atoms, which may have a substituent.

Example of A of (2) the linear or branched and/or cyclic hydrocarbon group having from 1 to 25 carbon atoms, which may have a substituent and/or an unsaturated bond include the following structures 1 to 44. The wave line shows a bonding site to the remaining sites of the structure of the general formula (5) disclosed in the present specification.

[Chem 23]

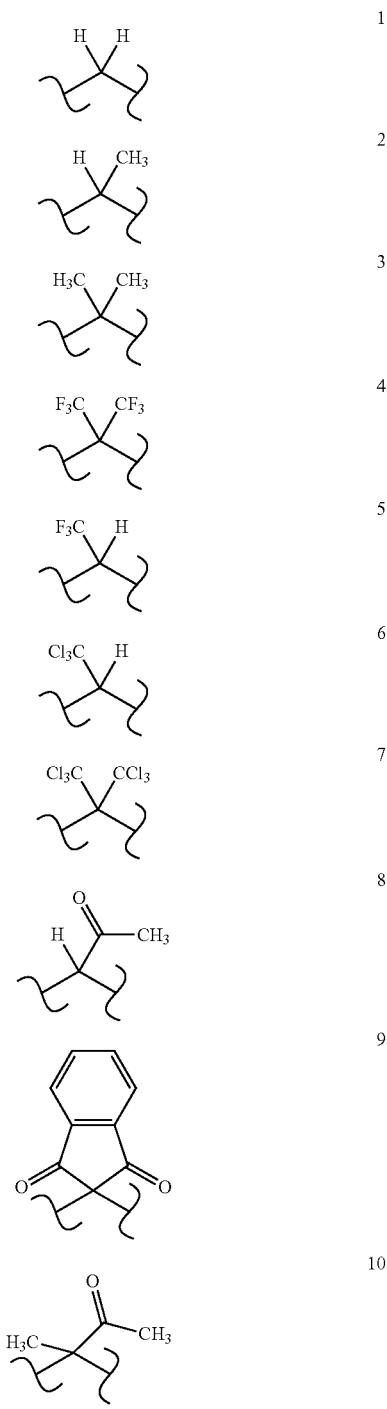

-continued
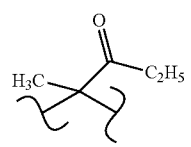
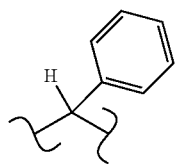
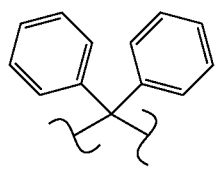
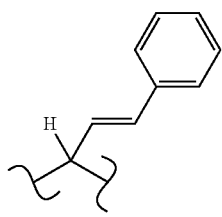
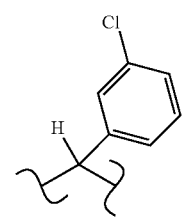
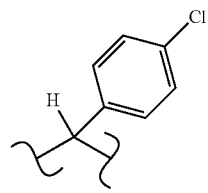
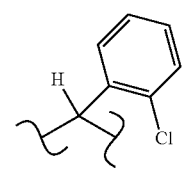
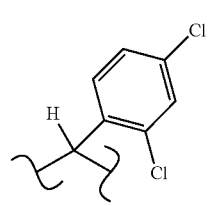
-continued
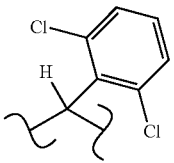
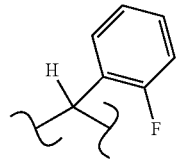
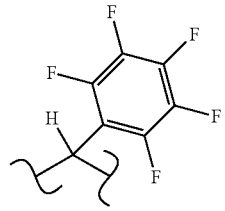
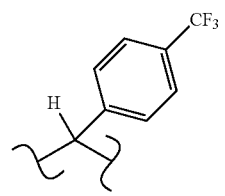
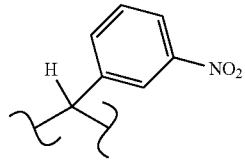
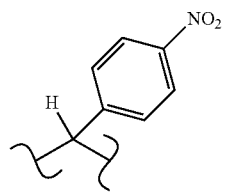
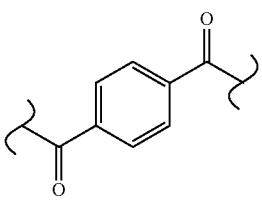
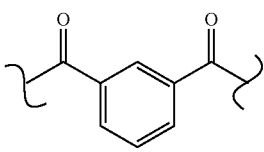

27 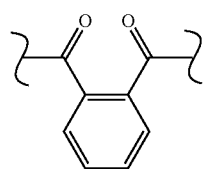

28 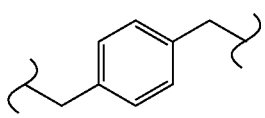

29 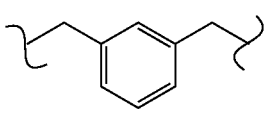

30 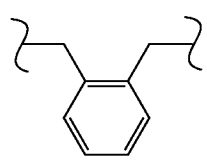

31 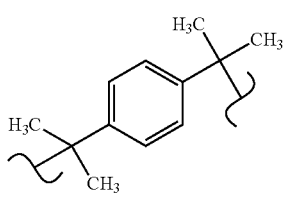

32 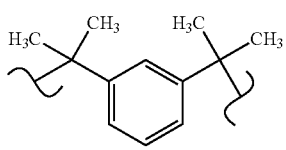

33 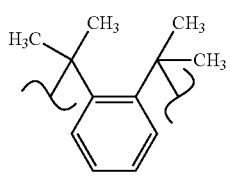

34 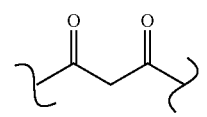

35 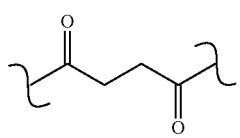

36 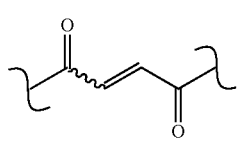

37 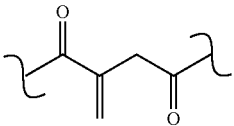

38 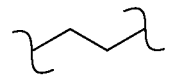

39 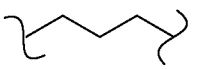

40 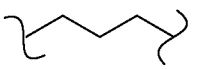

41 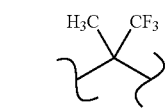

42 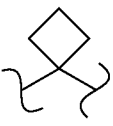

43 

44 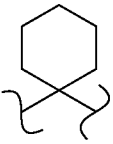

The structures 1 to 44 shown above may have a substituent, and examples of the substituent include the same substituents as exemplified in the aryl group.

Examples of A of (3) the arylene group having from 6 to 15 carbon atoms, which may have a substituent in the general formula (5) include phenylene group, naphthylene group and anthracenylene group.

Examples of A of (4) the heteroarylene group having from 2 to 15 carbon atoms, which may have a substituent in the general formula (5) include furylene group, theinylene group, pyronylene group, benzofurylene group, isobenzofurylene group, benzothienylene group, indolylene group, isoindolylene group, carbazoylene group, pyrizylene group, quinolylene group, isoquinolylene group, pyrazylene group and ferrocenylene group.

The arylene group and heteroarylene group may have a substituent, and examples of the substituent include the same substituents as exemplified in the aryl group.

A in the general formula (5) is a functional group or a hetero element, selected from the group consisting of —O—, —S—, —N($R^{12}$)—, —S(O)—, —C(O)—, —S(O)$_2$—, —P($R^{12}$)—, —($R^{12}$)P(O)— and —Si($R^{13}R^{14}$)—, wherein $R^{12}$ to $R^{14}$ each independently represent an alkyl group having from 1 to 6 carbon atoms, an alicyclic group having from 5 to 8 carbon atoms, an aralkyl group having from 7 to 12 carbon atoms, which may have a substituent, and/or an aryl group having from 6 to 10 carbon atoms, which may have a substituent. A is preferably —O—, —S—, —S(O)—, —S(O)$_2$— or —Si($R^{13}R^{14}$)—.

In the general formula (7), $R^{23}$ and $R^{24}$, and/or $R^{25}$ and $R^{26}$ may be combined with each other to form a 3- to 9-membered ring which may have a hetero element. In this case, examples of the hetero element include oxygen, nitrogen, phosphorus, sulfur, boron, silicon and metal elements capable of forming a metallocycle. A plurality of the hetero elements may be present in the ring B, and in this case, the hetero elements may be the same or different. The substituent may be present in the ring B, and the substituent may be present in the hetero element.

Specific examples of the 3- to 9-membered ring which may have a hetero element include cyclopropane ring, cyclobutane ring, cyclopentane ring, cyclohexane ring, cycloheptane ring, cyclooctane ring, benzene ring, naphthalene ring, norbornane ring, norbornene ring, decalin ring, furan ring, tetrahydrofuran ring, dioxolane ring, dioxane ring, dioxacyclohetane ring, trioxacycloheptane ring, lactone ring, lactam ring, morpholine ring, pyrropidine ring, piperidine ring, pyrazine ring, thiophene ring and tetrahydrothiophene ring.

Examples of the substituent include the same substituents as exemplified in the aryl group.

The hydroxy compound represented by the general formula (7) may form a polymer through the substituent or a carbon chain which is present in the 3- to 9-membered ring formed.

In the general formula (7), the ring B is a 3- to 8-membered ring which may have a hetero element. In this case, examples of the hetero element include oxygen, nitrogen, phosphorus, sulfur, boron, silicon and a metal element capable of forming a metallocycle. A plurality of the hetero elements may be present in the ring B, and in this case, the hetero elements may be the same or different. The substituent may be present in the ring B, or the substituent may be present in the hetero element.

Specific examples of the ring B include cyclopropane ring, cyclobutane ring, cyclopentane ring, cyclohexane ring, cycloheptane ring, cyclooctane ring, benzene ring, naphthalene ring, norbornane ring, norbornene ring, decalin ring, furan ring, tetrahydrofuran ring, dioxolane ring, dioxane ring, dioxacycloheptane ring, trioxacycloheptane ring, lactone ring, lactam ring, morpholine ring, pyrropidine ring, piperidine ring, pyradine ring, thiophene ring and tetrahydrothiophene ring.

Examples of the substituent include the same substituents as exemplified in the aryl group.

The hydroxy compound represented by the general formula (7) may form a polymer through the substituent or a carbon chain which is present in the ring B.

The diarylphenols represented by the general formula (4) are described in, for example, IP-T-2009-510006 and JP-A-2002-212121, the entire subject matter of which is incorporated herein by reference.

Examples of the preferred diarylphenols represented by the general formula (4) include 2,6-diphenylphenol, 2,6-di(4-fluorophenyl)phenol, 2,6-di(3,4-difluorophenyl)phenol, 2,6-di(3,4,5-trifluorophenyl)phenol, 2,6-diphenyl-4-methylphenol, 2,6-diphenyl-3,5-dimethylphenol, 2,6-di(2-methylphenyl)-3,5-dimethylphenol, 2,6-di(2-isopropylphenyl)-3,5-dimethylphenol, 2,6-di(α-naphthyl)-3,5-dimethylphenol, 3-phenyl-1,1'-binaphthyl-2-ol, 3-(4-fluorophenyl)-1,1'-binaphthyl-2-ol and 1,3-diphenyl-2-naphthol.

The bis(diarylphenol) compounds represented by the general formula (5) are described in, for example, Patent Document 5, the entire subject matter of which is incorporated herein by reference.

In the bis(diarylphenol) compounds represented by the general formula (5), examples of the preferred $R^8$, $R^9$, $R^{10}$ and $R^{11}$ include hydrogen atom, methyl group, ethyl group, isopropyl group, halogen atom (fluorine atom, chlorine atom), trifluoromethyl group, phenyl group, methoxy group and nitro group. More preferably, $R^8$, $R^9$, $R^{10}$ and $R^{11}$ are the same, and hydrogen atom is particularly preferred.

Examples of the preferred $Ar^3$, $Ar^4$, $Ar^5$ and $Ar^6$ include phenyl group, naphthyl group, 4-fluorophenyl group, 4-chlorophenyl group, 3-chlorophenyl group, 3,5-dichlorophenyl group, 4-methylphenyl group, 3-trifluoromethylphenyl group and 4-trifluoromethylphenyl group. More preferably, $Ar^3$, $Ar^4$, $Ar^5$ and $Ar^6$ are the same, and phenyl group is particularly preferred.

Examples of the preferred A include a single bond and the structures 1 to 44 described above. The single bond and the structures 1 to 5 are more preferred.

The biaryldiols represented by the general formula (6) are described in, for example, JP-T-2008-538101, the entire subject matter of which is incorporated herein by reference.

Examples of the preferred diarylphenols represented by the general formula (6) include the following compounds, but the invention is not limited to those.

[Chem. 24]

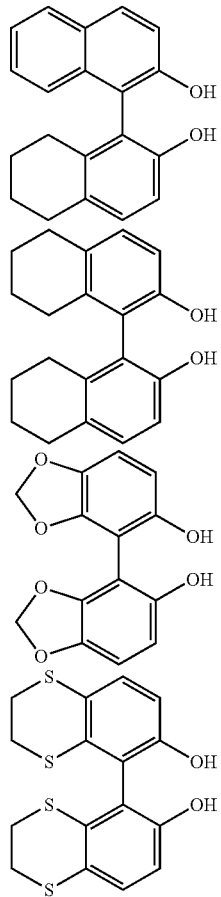

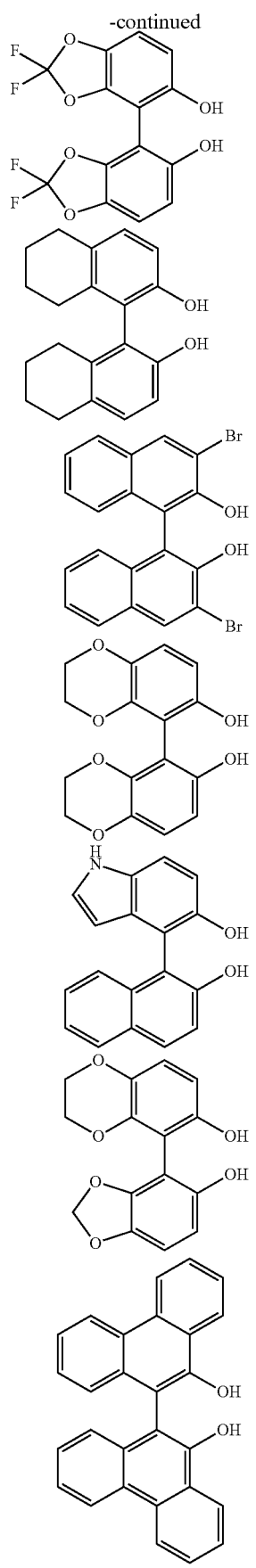
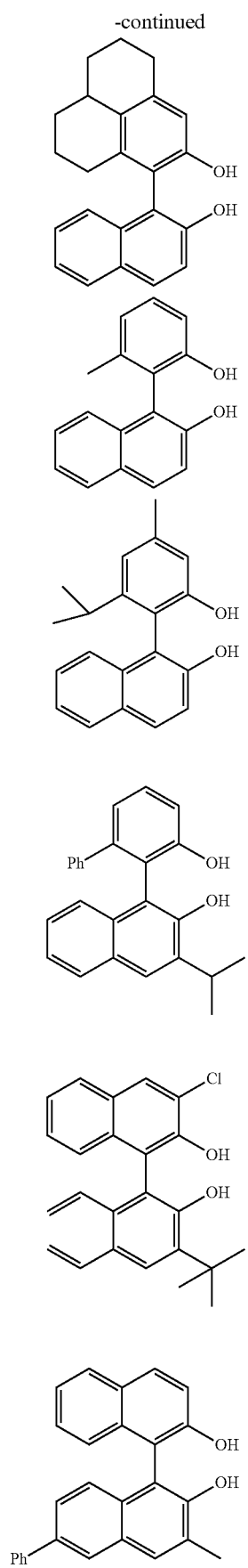

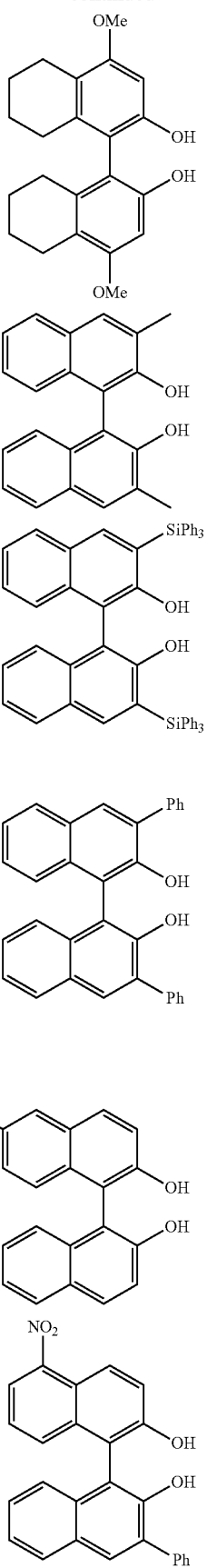
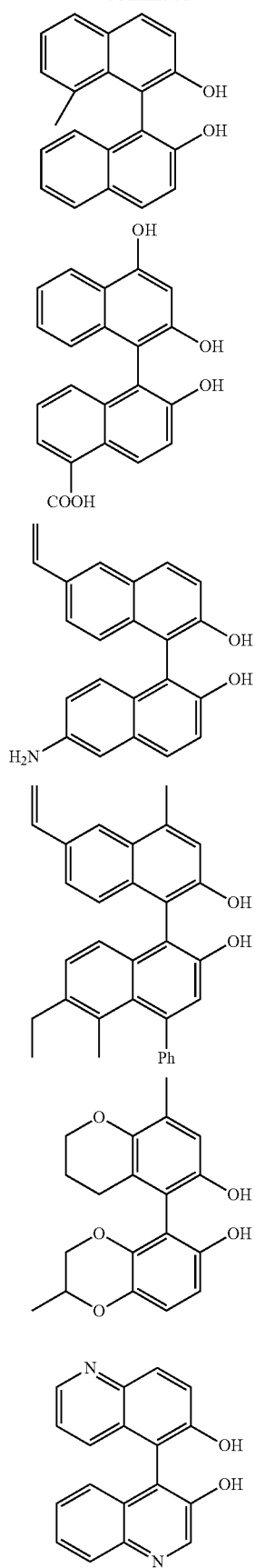

-continued
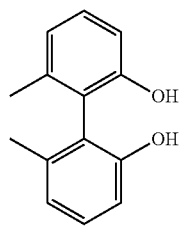
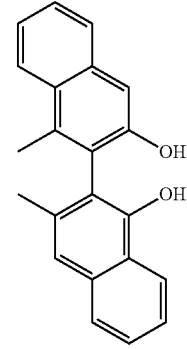
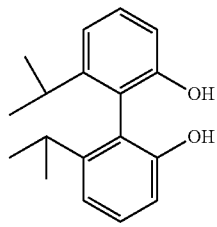
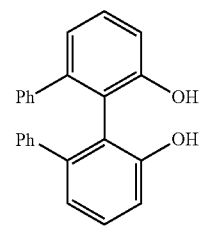
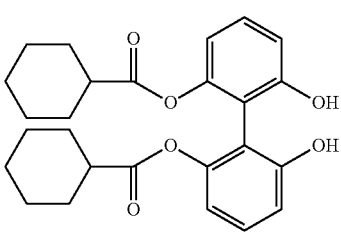
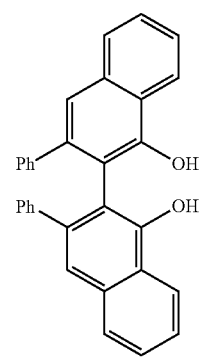
-continued
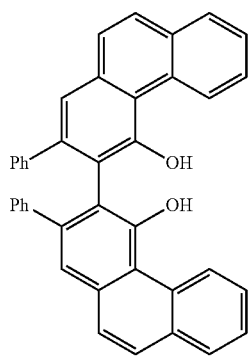
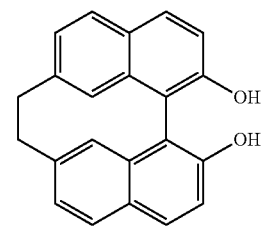
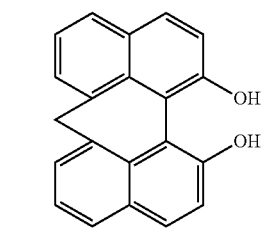
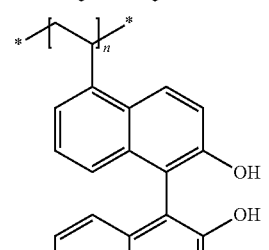
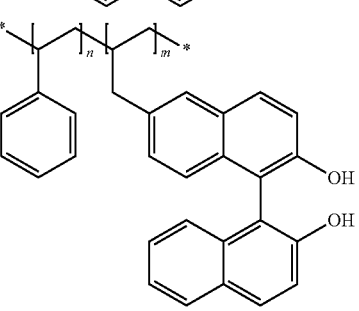
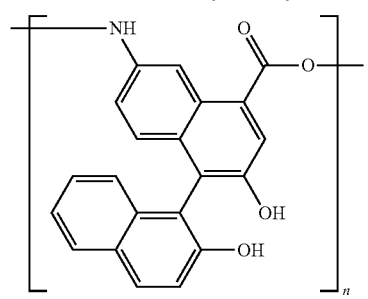

[Chem. 25]
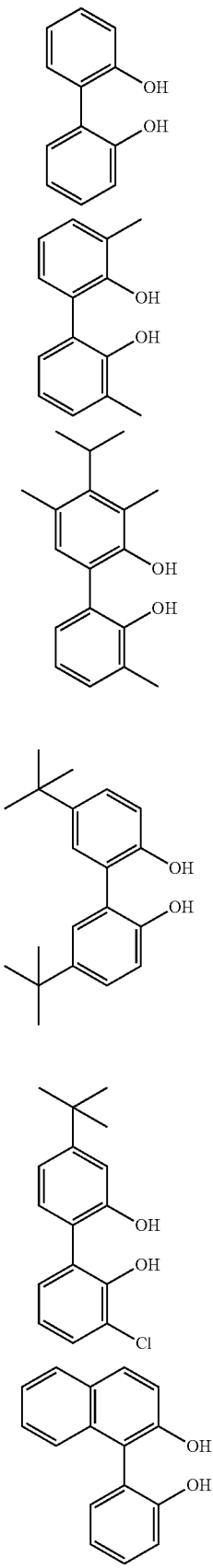
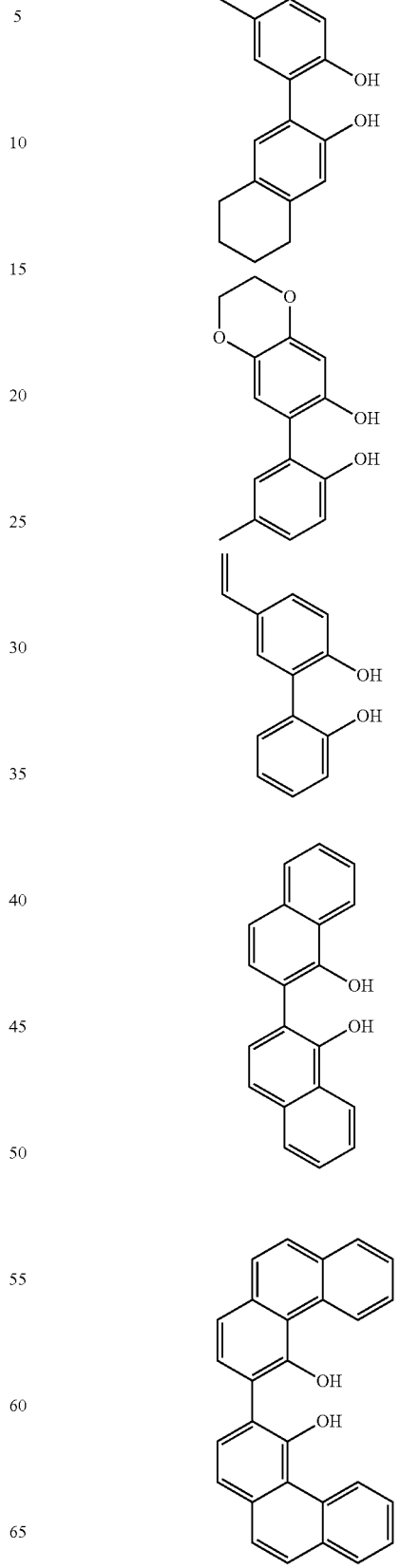

31
-continued
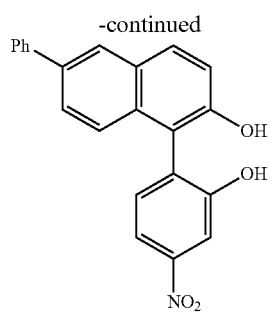
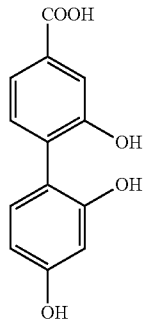
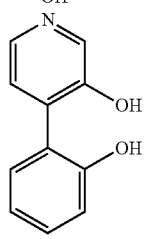
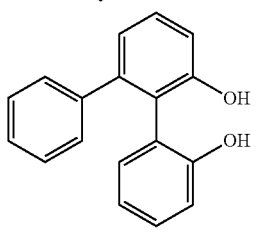
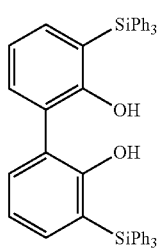
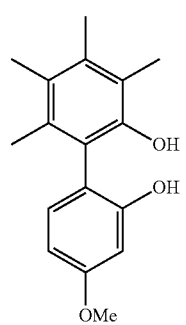
32
-continued
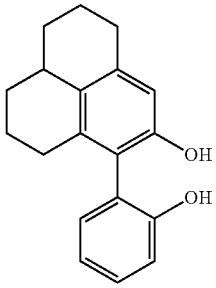
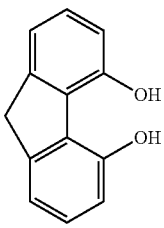
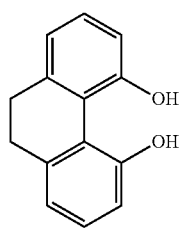
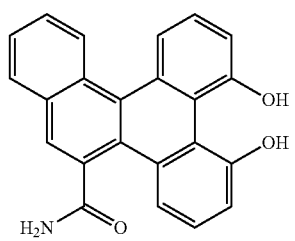
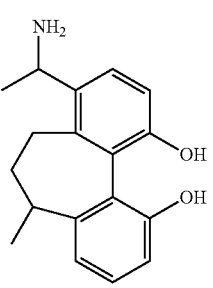

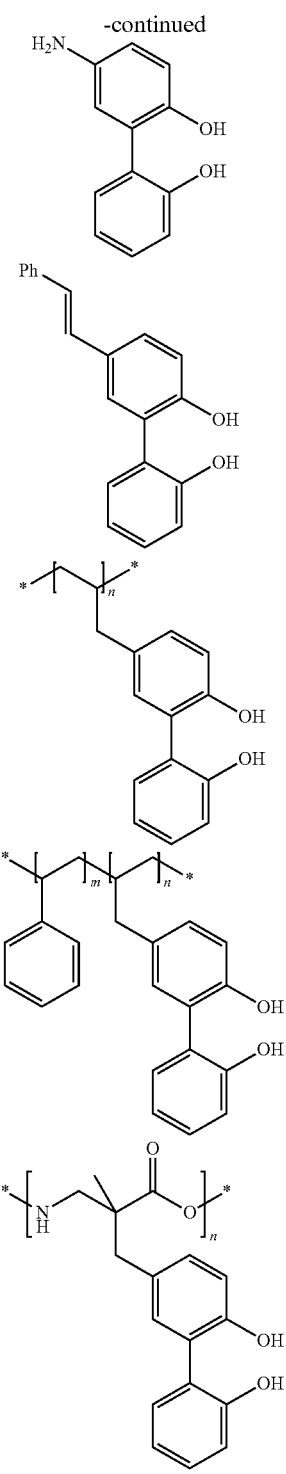

The dimethanols represented by the general formula (7) are described in, for example, U.S. Pat. No. 6,166,260, and Non-Patent Documents: Synlett, 1998, pp. 1291-1293; Tetrahedron: Asymmetry, 1991, Vol. 2, No. 12, pp. 1295-1304; CROATIA CHEMICA ACTA, 1996, 69, pp. 459-484; and Russian Chemical Bulletin, 2000, 49, pp. 460-465, the entire subject matter of which is incorporated herein by reference.

Examples of the preferred dimethanols represented by the general formula (7) include 2,2-dimethyl-α,α,α',α'-tetraphenyl-1,3-dioxolane-4,5-dimethanol (TADDOL) and 2,2-dimethyl-α,α,α',α'-tetra(1-naphthyl)-1,3-dioxolane-4,5-dimethanol (NAPHTADDOL).

The silanols represented by the general formula (8) are described in, for example, DE-A-102005023953 and WO2009/144906, the entire subject matter of which is incorporated here by reference.

Examples of the preferred silanols represented by the general formula (8) include trimethylsilanol, triethylsilanol, tert-butyldimethylsilanol and triphenylsilanol, but the invention is not limited to those.

The organoaluminum compound of the present invention is obtained by reacting at least one selected from organoaluminumoxy compounds represented by the general formulae (1) to (3) and at least one selected from the hydroxy compounds represented by the general formulae (4) to (9).

In this case, at least one selected from the hydroxy compounds represented by the general formulae (4) to (9) is preferably reacted in a proportion (aluminum atom: compound) of preferably from 0.25 to 10 equivalents, and more preferably from 0.5 to 3 equivalents, to at least one selected from organoaluminumoxy compounds represented by the general formulae (1) to (3) in an inert gas atmosphere.

The reaction can be conducted in the presence of an inert solvent. Examples of the solvent include an aliphatic hydrocarbon (such as hexane, heptane and octane), an alicyclic hydrocarbon (such as cyclohexane and methylcyclohexane), an aromatic hydrocarbon (such as benzene, toluene and xylene), an ether (such as diethyl ether, diisopropyl ether, dimethoxyethane, methyl tert-butyl ether, tetrahydrofuran, dioxane and dioxolane), and a halogenated hydrocarbon (such as dichloromethane, dichloroethane and chlorobenzene). Of those, the preferred solvent is an organic solvent such as toluene, heptane and dichloromethane. Those solvents are preferably used in the form of previously dried solvent or anhydrous solvent.

The amount of the solvent used is preferably from 1 to 10,000 times, and more preferably from 20 to 400 times, based on the amount of the hydroxy compound. The degree of polymerization of aluminoxane is preferably 2 or more.

The reaction temperature is preferably from about −60 to 100° C., more preferably from about −30 to 50° C., and particularly preferably from about −5 to 30° C. The reaction pressure is preferably 0.01 to 1 MPa, and more preferably 0.08 to 0.2 MPa. The reaction is conducted for preferably from about 0.25 to 30 hours, and more preferably from about 0.5 to 10 hours, while maintaining the above temperature, thereby the organoaluminum compound can be smoothly produced.

The organoaluminum compound of the present invention has the excellent effect as a catalyst in conducting an intramolecular reaction, particularly an intramolecular cyclization reaction.

The organoaluminum compound of the present invention can be used as a catalyst in conducting the reaction of cyclization-reacting citronellal in a racemic form or an optical active form to synthesize into isopulegol in a racemic form or an optical active form.

A method for producing isopulegol by selectively cyclizing citronellal using the organoaluminum compound of the present invention as a catalyst is conducted by the reaction shown in the following reaction scheme.

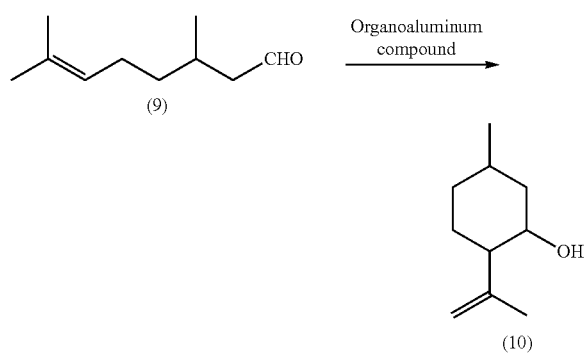

Furthermore, a method for producing optically active isopulegol by selectively cyclizing citronellal using the organoaluminum compound of the present invention as a catalyst is conducted by the reaction shown in the following reaction scheme.

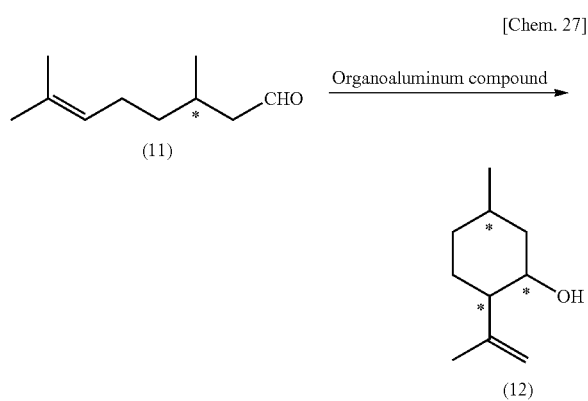

In the above reaction scheme, the "organoaluminum compound" has the same meaning as described before. Furthermore, in the formulae (11) and (12), * means an asymmetric carbon atom.

In the above reaction scheme, by selectively cyclizing the citronellal represented by the formula (9) or (11) in the presence of the organoaluminum compound of the present invention, isopulegol represented by the formula (10) or (12) is formed.

As the citronellal which is a raw material compound, the commercially available product can be directly used.

The amount of the organoaluminum compound used as a catalyst in the cyclization reaction of citronellal in the present invention is preferably from about 0.05 to 5% by mole, and more preferably from about 0.1 to 1% by mole, based on the citronellal.

With regard to the catalyst used in the cyclization reaction of citronellal in the present invention, the equivalent effect can be obtained by any method of a) a method of previously mixing at least one selected from the organoaluminumoxy compounds represented by the general formulae (1) to (3) and at least one selected from hydroxy compounds represented by the general formulae (4) to (9) in the reaction system to prepare a catalyst (organoaluminum compound), and then adding citronellal in the reaction system, and b) a method of individually adding a catalyst (organoaluminum compound) prepared by previously mixing the organoaluminumoxy compound and the hydroxy compound, and citronellal, respectively, at the time of the cyclization reaction.

The temperature of the cyclization reaction of citronellal is preferably from about −60 to 100° C., more preferably from about −30 to 50° C., and particularly preferably from about −5 to 20° C. The reaction pressure is preferably 0.01 to 1 MPa, and more preferably 0.08 to 0.2 MPa. By conducting the reaction for from about 0.25 to 30 hours, and more preferably from about 0.5 to 20 hours while maintaining the above temperature, isopulegol represented by the formula (10) or (12) can be smoothly obtained.

The cyclization reaction of citronellal in the present invention can be conducted in the absence of a solvent or in the presence of an inert solvent.

The solvent used is not particularly limited so long as it is a solvent that does not remarkably disturb the reaction. Examples of the solvent used include an aliphatic hydrocarbon (such as hexane, heptane and octane), an alicyclic hydrocarbon (such as cyclohexane and methylcyclohexane), an aromatic hydrocarbon (such as benzene, toluene and xylene), an ether (such as diethyl ether, diisopropyl ether, dimethoxyethane, methyl tert-butyl ether, tetrahydrofuran, dioxane and dioxolane) and a halogenated hydrocarbon (such as dichloromethane, dichloroethane and chlorobenzene). Of those, the preferred solvent is an organic solvent such as toluene, heptane and dichloromethane. Those solvents are preferably used in the form of a previously dried solvent or an anhydrous solvent.

The amount of the solvent used is preferably from about 0 to 20 times, and more preferably from 0.5 to 7 times, based on the amount of the citronellal.

In conducting the reaction, an acid compound or a base compound may be added. Specific examples of the acid compound include a mineral acid (such as hydrochloric acid and sulfuric acid), an organic acid (such as formic acid, acetic acid, propionic acid, citronellylic acid, geranylic acid and nerylic acid), and an organic acid anhydride (such as acetic anhydride, propionic anhydride, maleic anhydride, succinic anhydride and pivaloic anhydride). Specific examples of the base compound include an inorganic base (such as lithium hydroxide, sodium hydroxide, potassium hydroxide, lithium carbonate, sodium carbonate and potassium carbonate) and an organic base (such as trimethylamine and triethylamine).

The cyclization reaction is preferably conducted in an inert gas atmosphere such as nitrogen gas or argon gas for smooth progress of the cyclization reaction.

After completion of the reaction, the general post-treatment can be conducted. The isopulegol represented by the formula (10) or (12) is purified by simply conducting the treatment by distillation without conducting cryogenic separation, thereby high purity isopulegol can be obtained.

The residue after the distillation treatment is generally subjected to the treatment with an acid or an alkali, thereby removing impurities containing aluminum or the like, and after that, it is subjected to crystallization or the like. As a result, the hydroxy compound can be reutilized as a ligand.

On the other hand, in the organoaluminum compound of the present invention, an organoaluminum compound which is sparingly soluble in a solvent is removed by filtration after completion of the reaction, and it can be directly used in the subsequent reaction.

The ligand of all of the organoaluminum compounds is recovered after deactivation of catalyst, and then it can again be reutilized as the catalyst.

EXAMPLES

The present invention is described in detail below by reference to Examples and Comparative Examples, but the invention is not construed as being limited thereto, and may be modified as long as it does not deviate the scope of the present invention.

Measurement of products in Synthesis Examples and Examples was conducted using the following instruments and apparatus.

Nuclear Magnetic Resonance Spectrum
$^1$H-NMR: Oxford 300 MHz, FT-NMR, (300 MHz) (manufactured by Varian)
Gas chromatograph: GC-2010 Gas Chromatograph, manufactured by Shimadzu Corporation
Column:
Measurement of addition rate: DB-WAX (0.25 mm×30 m), manufactured by Agilent
Measurement of optical purity: beta-DEX-225 (0.25 mm×30 m), manufactured by Supelco, and beta-DEX-325 (0.25 mm×30 m), manufactured by Supelco
Detector: FID Optical purity of each citronellal used in the present invention is as follows.
d-Citronellal: 97.8% e.e.
l-Citronellal: 96.6% e.e.
Racemic form citronellal: 0.74% e.e.
Aluminoxane 10 wt % solution was titrated with EDTA 0.1N solution, and 8 to 12 wt % solution thereof was used.

Example 1-1

Figure 2:
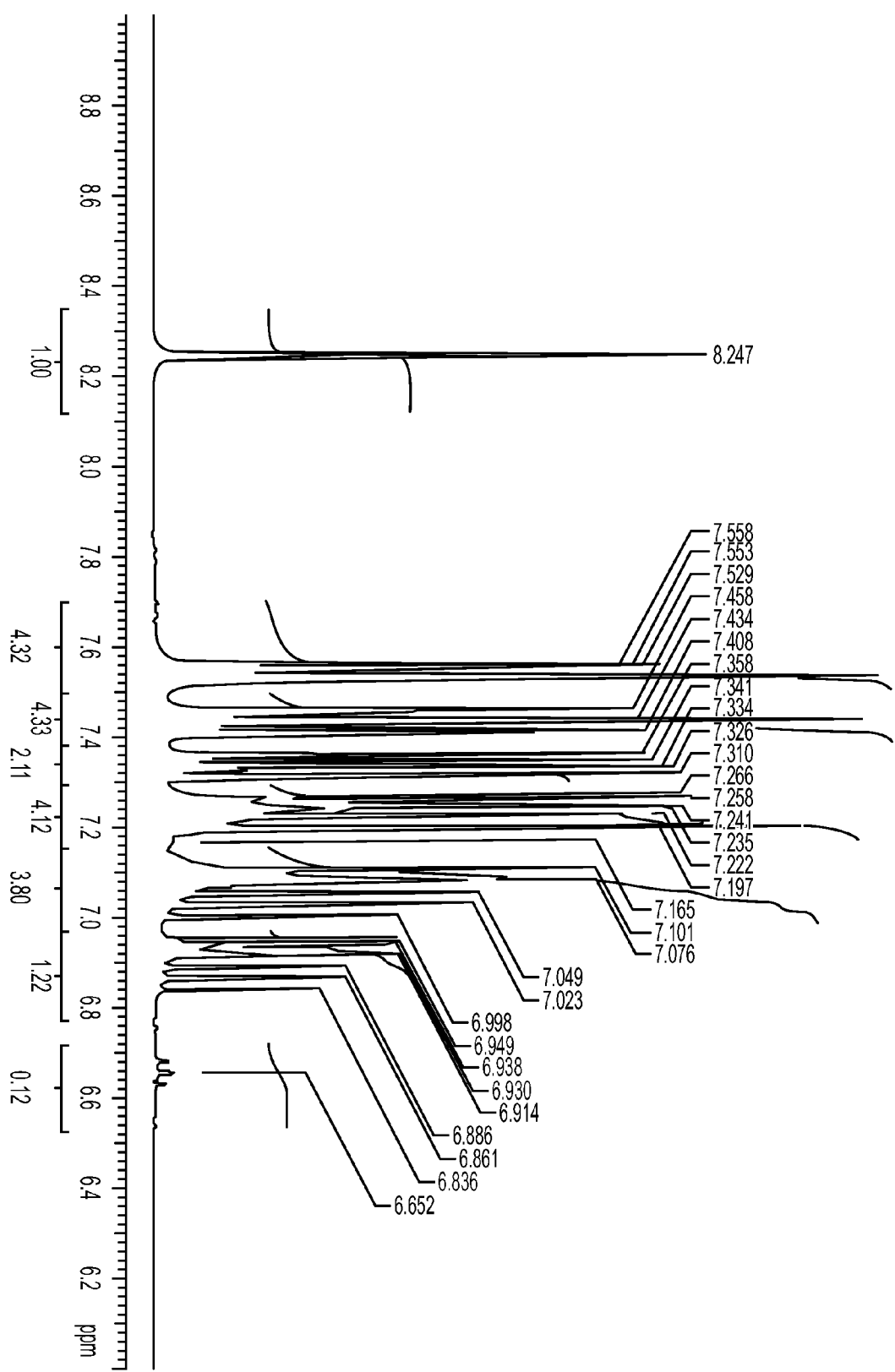
FIG. 2 is an enlarged view at low magnetic field side of NMR spectrum of 2,6-diphenylphenol and methylaluminoxane reactant.
Figure 3:
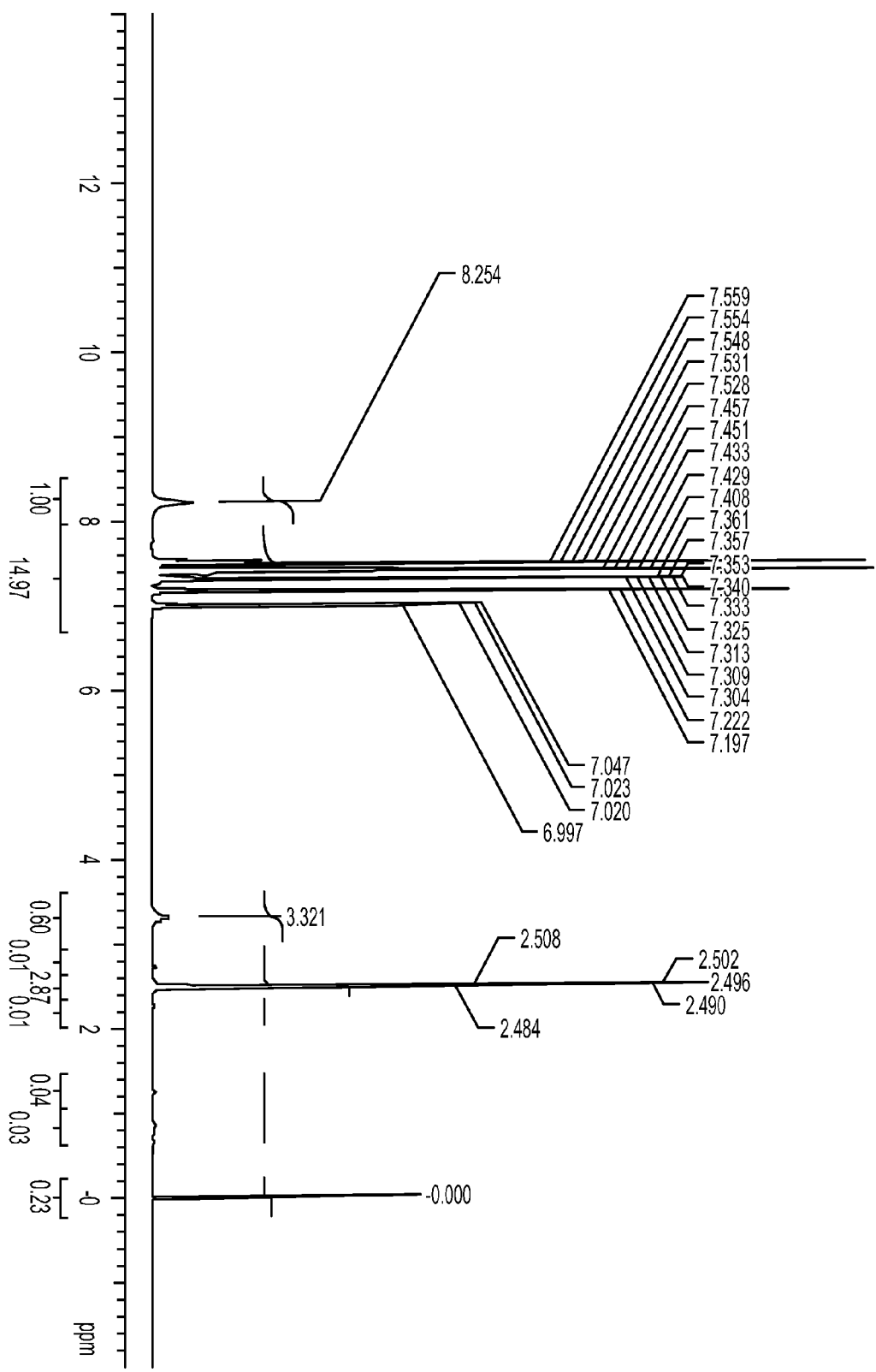
FIG. 3 is a view showing NMR spectrum of 2,6-diphenylphenol.
Figure 4:
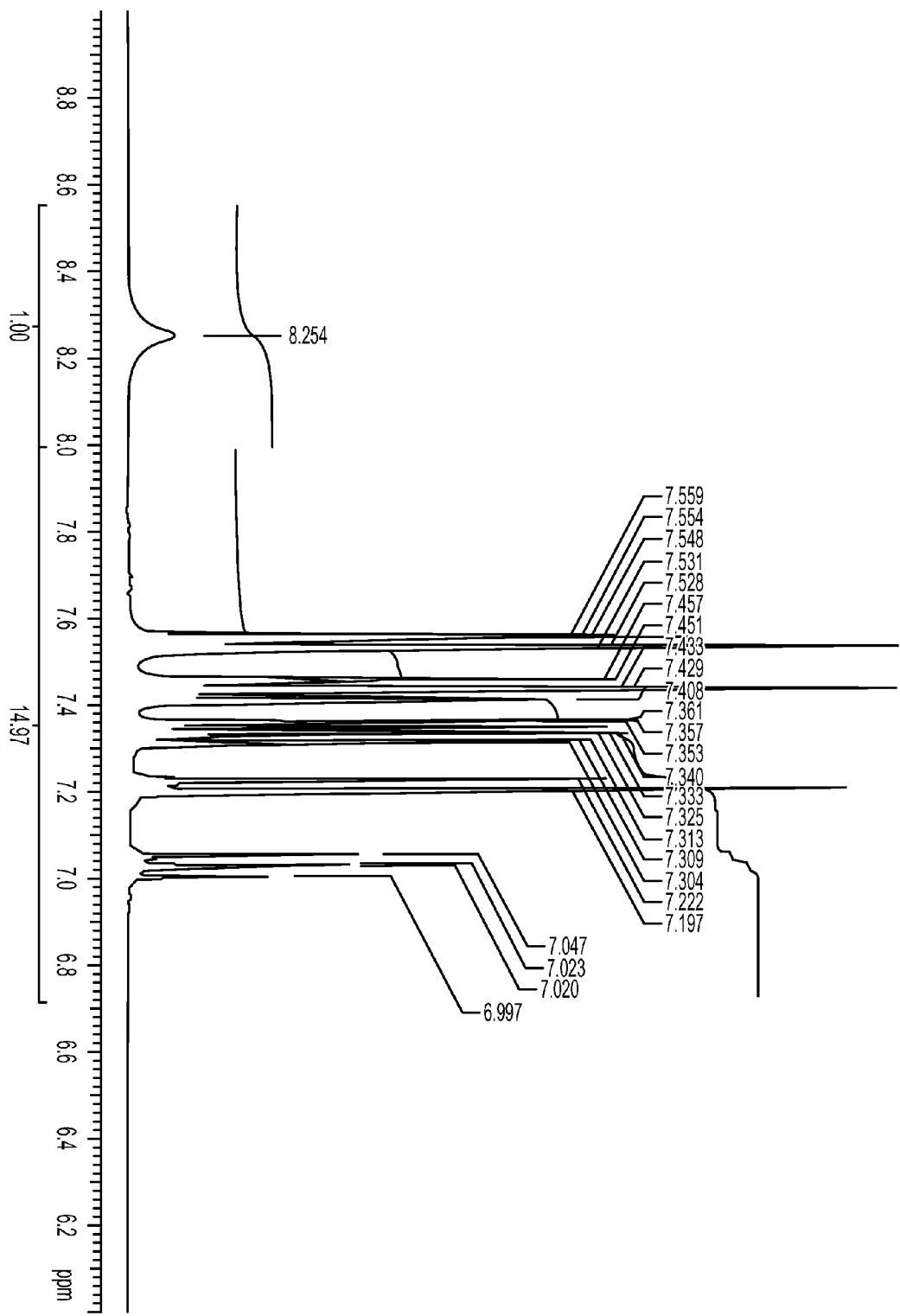
FIG. 4 is an enlarged view at low magnetic field side of NMR spectrum of 2,6-diphenylphenol.

Preparation of Organoaluminum Compound 493 mg (2.0 mmol) of 2,6-diphenylphenol was placed in a 50 ml Schlenk flask under a nitrogen atmosphere. After nitrogen substitution, 10 ml of heptane and 0.58 ml (10% by mass, 1.00 mmol) of a methylaluminoxane-toluene solution were sequentially added to the flask, and the resulting mixture was stirred at room temperature overnight. The solvent was distilled away to obtain a white solid. The solid obtained was dissolved in DMSO-$d_6$, and it was measured with $^1$H-NMR. Peak of aluminum complex in addition to diphenylphenol was confirmed. NMR charts (FIG. 1) of the ligand and the catalyst and an enlarged view of low magnetic field side (FIG. 2) are shown. As reference views, NMR chart (FIG. 3) of the ligand (2,6-diphenylphenol) and an enlarged view (FIG. 4) of low magnetic field side are shown.

Example 1-2

Synthesis of l-Isopulegol 4.6 ml of toluene was added to the organoaluminum compound synthesized according to Example 1-1 under a nitrogen atmosphere, and the temperature in the system was cooled to 0 to 5° C. 1.54 g (10 mmol) of d-citronellal was added dropwise to the resulting mixture, followed by stirring at 0 to 5° C. overnight. After completion of the reaction, 2 ml of water was added to the reaction mixture, and an organic layer was analyzed with gas chromatography. As a result, substrate conversion was 70.5%, isopulegol conversion was 814%, and the ratio of l-n-isopulegol to the other isomers was 97.1:2.9.

Example 2-1

Preparation of Organoaluminum Compound 197 mg (0.80 mmol) of 2,6-diphenylphenol was placed in a 50 ml Schlenk flask. After nitrogen substitution, 9.3 ml of toluene and 0.12 ml (10% by mass, 0.20 mmol) of a methylaluminoxane-toluene solution were sequentially added to the flask, and the resulting mixture was stirred at room temperature for 1 hour, thereby obtaining a catalyst solution.

Example 2-2

Synthesis of l-Isopulegol

The catalyst solution obtained in Example 2-1 was cooled to 0 to 5° C., and 3.09 g (20.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 59.7%, isopulegol conversion was 87.0%, and the ratio of l-n-isopulegol to the other isomers was 98.1:1.9.

Example 3-1

Preparation of Organoaluminum Compound 197 mg (0.60 mmol) of 2,6-diphenylphenol was placed in a 50 ml Schlenk flask. After nitrogen substitution, 4.6 ml of toluene and 0.17 ml (10% by mass, 0.30 mmol) of a methylaluminoxane-toluene solution were sequentially added to the flask, and the resulting mixture was stirred at room temperature for 1 hour, thereby obtaining a catalyst solution.

Example 3-2

Synthesis of l-Isopulegol

The catalyst solution obtained in Example 3-1 was cooled to 0 to 5° C., and 1.54 g (10.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 82.2%, isopulegol conversion was 71.5%, and the ratio of l-n-isopulegol to the other isomers was 95.5:4.5.

Example 4-1

Preparation of Organoaluminum Compound 370 mg (1.50 mmol) of 2,6-diphenylphenol was placed in a 50 ml Schlenk flask. After nitrogen substitution, 4.6 ml of toluene and 0.17 ml (10% by mass, 0.30 mmol) of a methylaluminoxane-toluene solution were sequentially added to the flask, and the resulting mixture was stirred at room temperature for 1 hour, thereby obtaining a catalyst solution.

Example 4-2

Synthesis of l-Isopulegol

The catalyst solution obtained in Example 4-1 was cooled to 0 to 5° C., and 1.54 g (10.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate

Example 5-1

Preparation of Organoaluminum Compound 148 mg (0.60 mmol) of 2,6-diphenylphenol was placed in a 50 ml Schlenk flask. After nitrogen substitution, 4.6 ml of toluene and 0.17 ml (10% by mass, 0.30 mmol) of a methylaluminoxane-toluene solution were sequentially added to the flask, and the resulting mixture was stirred at 40° C. overnight, thereby obtaining a catalyst solution.

Example 5-2

Synthesis of l-Isopulegol

The catalyst solution obtained in Example 5-1 was cooled to 0 to 5° C., and 1.54 g (10.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 64.8%, isopulegol conversion was 84.8%, and the ratio of l-n-isopulegol to the other isomers was 98.1:1.9.

Example 6-1

Preparation of Organoaluminum Compound 370 mg (1.50 mmol) of 2,6-diphenylphenol was placed in a 50 ml Schlenk flask. After nitrogen substitution, 4.6 ml of toluene and 0.17 ml (10% by mass, 0.30 mmol) of a methylaluminoxane-toluene solution were sequentially added to the flask, and the resulting mixture was stirred at 40° C. overnight, thereby obtaining a catalyst solution.

Example 6-2

Synthesis of l-Isopulegol

The catalyst solution obtained in Example 6-1 was cooled to 0 to 5° C., and 1.54 g (10.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 22.3%, isopulegol conversion was 84.2%, and the ratio of l-n-isopulegol to the other isomers was 97.6:2.4.

Example 7-1

Preparation of Organoaluminum Compound 148 mg (0.60 mmol) of 2,6-diphenylphenol was placed in a 50 ml Schlenk flask. After nitrogen substitution, 4.6 ml of toluene and 0.17 ml (10% by mass, 0.30 mmol) of a methylaluminoxane-toluene solution were sequentially added to the flask, and the resulting mixture was stirred at room temperature for 1 hour, thereby obtaining a catalyst solution.

Example 7-2

Synthesis of d-Isopulegol

The catalyst solution obtained in Example 7-1 was cooled to 0 to 5° C., and 1.54 g (10.0 mmol) of l-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 89.2%, isopulegol conversion was 88.1%, and the ratio of l-n-isopulegol to the other isomers was 96.9:3.1.

Example 8-1

Preparation of Organoaluminum Compound 148 mg (0.60 mmol) of 2,6-diphenylphenol was placed in a 50 ml Schlenk flask. After nitrogen substitution, 4.6 ml of methylene chloride and 0.17 ml (10% by mass, 0.30 mmol) of a methylaluminoxane-toluene solution were sequentially added to the flask, and the resulting mixture was stirred at 40° C. overnight, thereby obtaining a catalyst solution.

Example 8-2

Synthesis of l-Isopulegol

The catalyst solution obtained in Example 8-1 was cooled to 0 to 5° C., and 1.54 g (10.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 98.8%, isopulegol conversion was 93.3%, and the ratio of l-n-isopulegol to the other isomers was 98.2:1.8.

Example 9-1

Preparation of Organoaluminum Compound 400 mg (0.60 mmol) of (S,S)-2,2-dimethyl-$\alpha,\alpha,\alpha',\alpha'$-tetra(1-naphthyl)-1,3-dioxolane-4,5-dimethanol (hereinafter referred to as (S,S)-1-Naphthyl TADOL or (S,S)-1-NAPH-TADDOL) was placed in a 50 ml Schlenk flask. After nitrogen substitution, 9.3 ml of toluene and 0.35 ml (10% by mass, 0.60 mmol) of a methylaluminoxane-toluene solution were sequentially added to the flask, and the resulting mixture was stirred at room temperature for 1 hour, thereby obtaining a catalyst solution.

Example 9-2

Synthesis of l-Isopulegol

The catalyst solution obtained in Example 9-1 was cooled to 0 to 5° C., and 3.09 g (20.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate

--- conversion was 81.9%, isopulegol conversion was 82.0%, and the ratio of l-n-isopulegol to the other isomers was 96.5:3.5.

conversion was 94.8%, isopulegol conversion was 91.8%, and the ratio of l-n-isopulegol to the other isomers was 90.8:9.2.

Example 10-1

Preparation of Organoaluminum Compound 275 mg (1.60 mmol) of (R)-2,2'-dihydroxy-1,1'-binaphthyl (hereinafter referred to as (R)-BINOL) was placed in a 50 ml Schlenk flask. After nitrogen substitution, 9.3 ml of toluene and 0.35 ml (10% by mass, 0.60 mmol) of a methylaluminoxane-toluene solution were sequentially added to the flask, and the resulting mixture was stirred at 40° C. overnight, thereby obtaining a catalyst solution.

Example 10-2

Synthesis of l-Isopulegol

The catalyst solution obtained in Example 10-1 was cooled to 0 to 5° C., and 3.09 g (20.0 mmol) of d-citronellal was added dropwise to the solution, followed by stirring at 0 to 5° C. overnight. After completion of the reaction, 2 ml of water was added to the reaction mixture, and an organic layer was analyzed with gas chromatography. As a result, substrate conversion was 83.7%, isopulegol conversion was 84.8%, and the ratio of l-n-isopulegol to the other isomers was 87.8:12.2.

Example 11-1

Preparation of Organoaluminum Compound 275 mg (1.60 mmol) of (R)-BINOL was placed in a 50 ml Schlenk flask. After nitrogen substitution, 9.3 ml of toluene and 0.35 ml (10% by mass, 0.60 mmol) of a methylaluminoxane-toluene solution were sequentially added to the flask, and the resulting mixture was stirred at 40° C. overnight, thereby obtaining a catalyst solution.

Example 11-2

Synthesis of l-Isopulegol (Optical Resolution)

The catalyst solution obtained in Example 11-1 was cooled to 0 to 5° C., and 3.09 g (20.0 mmol) of racemic form-citronellal was added dropwise to the solution, followed by stirring at 0 to 5° C. for 1.5 hours. After completion of the reaction, 2 ml of water was added to the reaction mixture, and an organic layer was analyzed with gas chromatography. As a result, substrate conversion was 52.5%, isopulegol conversion was 89.9%, and the ratio of l-n-isopulegol to the other isomers was 86.8:13.2. Enantioselectivity of l-n-isopulegol in the system was 44.3%, and enantioselectivity of l-citronellal was 30.2%.

Example 12-1

Preparation of Organoaluminum Compound 400 mg (0.60 mmol) of (S,S)-1-NAPHTADDOL was placed in a 50 ml Schlenk flask. After nitrogen substitution, 9.3 ml of toluene and 0.35 ml (10% by mass, 0.60 mmol) of a methylaluminoxane-toluene solution were sequentially added to the flask, and the resulting mixture was stirred at 40° C. overnight, thereby obtaining a catalyst solution.

Example 12-2

Synthesis of l-Isopulegol (Optical Resolution)

The catalyst solution obtained in Example 12-1 was cooled to 0 to 5° C., and 3.09 g (20.0 mmol) of racemic form-citronellal was added dropwise to the solution, followed by stirring at 0 to 5° C. for 9 hours. After completion of the reaction, 2 ml of water was added to the reaction mixture, and an organic layer was analyzed with gas chromatography. As a result, substrate conversion was 51.1%, isopulegol conversion was 85.7%, and the ratio of l-n-isopulegol to the other isomers was 89.0:11.0. Enantioselectivity of l-n-isopulegol in the system was 16.6%, and enantioselectivity of l-citronellal was 10.4%.

Example 13-1

Preparation of Organoaluminum Compound 286 mg (1.00 mmol) of (R)-BINOL was placed in a 50 ml Schlenk flask under a nitrogen atmosphere. After nitrogen substitution, 11 ml of heptane and 0.58 ml (10% by mass, 1.00 mmol) of a methylaluminoxane-toluene solution were sequentially added to the flask, and the resulting mixture was stirred at 40° C. for 16 hours. The solvent was distilled away to obtain a white solid (organoaluminum compound).

Example 13-2

Synthesis of l-Isopulegol 6 ml of heptane was added to the solid obtained in Example 13-1 under a nitrogen atmosphere. The temperature in the system was cooled to 0 to 5° C., and 1.54 g (10 mmol) of d-citronellal was added dropwise to the mixture, followed by stirring at 0 to 5° C. for 2 hours. The reaction liquid was allowed to stand for about 30 minutes, and 4.5 ml of a supernatant was collected with a syringe. 2 ml of water was added, and an organic layer was analyzed with gas chromatography. As a result, substrate conversion was 99.6%, isopulegol conversion was 96.8%, and the ratio of l-n-isopulegol to the other isomers was 93.4:6.6.

As a second reaction, 4.5 ml of heptane was added to the residue in the Schlenk, and the inside of the system was again cooled to 0 to 5° C. while restarting the stirring. 1.54 g (10 mmol) of d-citronellal was added dropwise to the Schlenk. After completion of the dropwise addition, a sample was collected and analyzed with gas chromatography. Stirring was further conducted at 0 to 5° C. for 3 hours. The reaction liquid was allowed to stand for about 30 minutes, and 4.5 ml of a supernatant was collected with a syringe. 2 ml of water was added, and an organic layer was analyzed with gas chromatography.

In the second reaction, substrate conversion in the system just after the dropwise addition was 38.2%, substrate conversion after the reaction for 3 hours was 97.8%, isopulegol selectivity was 95.7%, and the ratio of l-n-isopulegol to the other isomers was 94.8:5.2.

As a third reaction, 4.5 ml of heptane was added to the residue in the Schlenk, and the inside of the system was again cooled to 0 to 5° C. while restarting the stirring. 1.54 g (10 mmol) of d-citronellal was added dropwise to the Schlenk. After completion of the dropwise addition, a sample was collected and analyzed with gas chromatography. Stirring was further conducted at 0 to 5° C. for 3 hours. 2 ml of water was added to 4 to 5 ml of a supernatant of the reaction liquid to complete the reaction phase, and an organic layer was analyzed with gas chromatography.

In the third reaction, substrate conversion in the system just after the dropwise addition was 27.8%, substrate conversion after the reaction for 3 hours was 96.9%, isopulegol selectivity was 95.4%, and the ratio of l-n-isopulegol to the other isomers was 95.1:4.9.

As a forth reaction, 4.5 ml of heptane was added to the residue in the Schlenk, and the inside of the system was again cooled to 0 to 5° C. while restarting the stirring. 1.54 g (10 mmol) of d-citronellal was added dropwise to the Schlenk. After completion of the dropwise addition, a sample was collected and analyzed with gas chromatography. Stirring was further conducted at 0 to 5° C. for 5 hours. 2 ml of water was added to 4 to 5 ml of a supernatant of the reaction liquid to complete the reaction phase, and an organic layer was analyzed with, gas chromatography.

In the fourth reaction, substrate conversion in the system just after the dropwise addition was 31.1%, substrate conversion after the reaction for 5 hours was 92.9%, isopulegol selectivity was 94.8%, and the ratio of l-n-isopulegol to the other isomers was 95.5:4.5.

As a fifth reaction, 4.5 ml of heptane was added to the residue in the Schlenk, and the inside of the system was again cooled to 0 to 5° C. while restarting the stirring. 1.54 g (10 mmol) of d-citronellal was added dropwise to the Schlenk. After completion of the dropwise addition, a sample was collected and analyzed with gas chromatography. Stirring was further conducted at 0 to 5° C. for 7 hours. 2 ml of water was added to the reaction liquid to complete the reaction, and an organic layer was analyzed with gas chromatography.

In the fifth reaction, substrate conversion in the system just after the dropwise addition was 25.4%, substrate conversion after the reaction for 7 hours was 90.9%, isopulegol selectivity was 92.9%, and the ratio of l-n-isopulegol to the other isomers was 94.5:5.5.

The invention claimed is:

1. An organoaluminum compound obtained by reacting at least one organoaluminumoxy compound selected from the group consisting of chain aluminoxanes represented by the following general formula (1), cyclic aluminoxanes represented by the following general formula (2) and bis(dialkylaluminumoxy)alkylboranes represented by the following general formula (3), with at least one hydroxy compound selected from the group consisting of diarylphenols represented by the following general formula (4), bis(diarylphenol) compounds represented by the following general formula (5), biaryldiols represented by the following general formula (6), dimethanols represented by the following general formula (7) and silanols represented by the following general formula (8):

[Chem. 1]

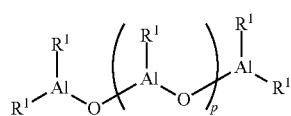
(1)

wherein $R^1$ represents an alkyl group having from 1 to 6 carbon atoms, an alicyclic group having from 5 to 8 carbon atoms, or an aralkyl group having from 7 to 12 carbon atoms, which may have a substituent, and the plural $R^1$ may be the same or different; and p is an integer of from 0 to 40;

[Chem. 2]

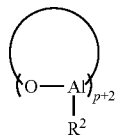
(2)

wherein $R^2$ represents an alkyl group having from 1 to 6 carbon atoms, an alicyclic group having from 5 to 8 carbon atoms, or an aralkyl group having from 7 to 12 carbon atoms, which may have a substituent; and p is an integer of from 0 to 40;

[Chem. 3]

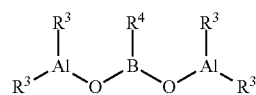
(3)

wherein $R^3$ represents an alkyl group having from 1 to 6 carbon atoms, an alicyclic group having from 5 to 8 carbon atoms, or an aralkyl group having from 7 to 12 carbon atoms, which may have a substituent, and the plural $R^3$ may be the same or different; and $R^4$ represents an alkyl group having from 1 to 6 carbon atoms, an alicyclic group having from 5 to 8 carbon atoms, or an aralkyl group having from 7 to 12 carbon atoms, which may have a substituent;

[Chem. 4]

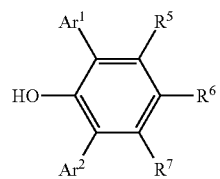
(4)

wherein $Ar^1$ and $Ar^2$ each independently represent an aryl group having from 6 to 15 carbon atoms, which may have a substituent, or a heteroaryl group having from 2 to 15 carbon atoms, which may have a substituent; $R^5$, $R^6$ and $R^7$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; and $R^5$ and $R^6$, or $R^6$ and $R^7$ may be combined with each other to form a condensed benzene ring, a condensed substituted-benzene ring, trimethylene group, tetramethylene group, pentamethylene group, methylenedioxy group, ethylenedioxy group or trimethylenedioxy group;

[Chem. 5]

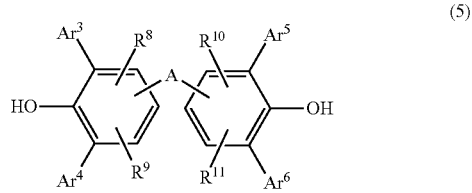
(5)

wherein $Ar^3$, $Ar^4$, $Ar^5$ and $Ar^6$ each independently represent an aryl group having from 6 to 15 carbon atoms, which may have a substituent, or a heteroaryl group having from 2 to 15 carbon atoms, which may have a substituent; $R^8$, $R^9$, $R^{10}$ and $R^{11}$ each independently represent hydrogen atom, an alkyl group having from 1 to 8 carbon atoms, an alicyclic group having from 5 to 8 carbon atoms, a perfluoroalkyl group having from 1 to 4 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may have a substituent, a dialkylamino group having from 2 to 8 carbon atoms, a thioalkoxy group having from 1 to 4 carbon atoms, a nitro group or a polymer chain; $R^8$ and $R^9$, and/or $R^{10}$ and $R^{11}$ may be combined with each other to form a condensed benzene ring, a condensed substituted-benzene ring, trimethylene group, tetramethylene group, pentamethylene group, methylenedioxy group, ethylenedioxy group or trimethylenedioxy group; and $R^8$ or $R^9$ and/or $R^{10}$ or $R^{11}$ may be combined with A to form a cyclic aromatic ring or a non-aromatic ring; and A is (1) a single bond, (2) a linear or branched and/or cyclic hydrocarbon group having from 1 to 25 carbon atoms, which may have a substituent and/or an unsaturated bond, (3) an arylene group having from 6 to 15 carbon atoms, which may have a substituent, (4) a heteroarylene group having from 2 to 15 carbon atoms, which may have a substituent, (5) a functional group or a hetero element, which is selected from the group consisting of —O—, —S—, —N($R^{12}$)—, —S(O)—, —C(O)—, —S(O)$_2$—, —P($R^{12}$)—, —($R^{12}$)P(O)— and —Si($R^{13}R^{14}$)—, wherein $R^{12}$ to $R^{14}$ each independently represent an alkyl group having from 1 to 6 carbon atoms, an alicyclic group having from 5 to 8 carbon atoms, an aralkyl group having from 7 to 12 carbon atoms, which may have a substituent, or an aryl group having from 6 to 10 carbon atoms, which may have a substituent;

[Chem. 6]

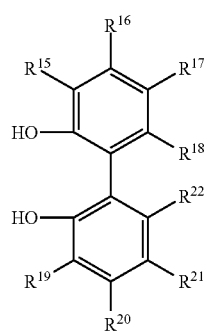
(6)

wherein $R^{15}$, $R^{16}$, $R^{17}$, $R^{18}$, $R^{19}$, $R^{20}$, $R^{21}$ and $R^{22}$ each independently represent hydrogen atom, an alkyl group having from 1 to 8 carbon atoms, a perfluoroalkyl group having from 1 to 4 carbon atoms, an alkoxy group having from 1 to 8 carbon atoms, an alicyclic group having from 5 to 8 carbon atoms, an aralkyl group having from 7 to 12 carbon atoms, which may have a substituent, a halogen atom, an organosilyl group, an aryl group having from 6 to 15 carbon atoms, which may has a substituent, a dialkylamino group having from 2 to 8 carbon atoms, a thioalkoxy group having from 1 to 4 carbon atoms, a nitro group or a polymer chain, and at least one pair of $R^{15}$ and $R^{16}$, $R^{16}$ and $R^{17}$, $R^{17}$ and $R^{18}$, $R^{15}$ and $R^{22}$, $R^{19}$ and $R^{20}$, $R^{20}$ and $R^{21}$, and $R^{21}$ and $R^{22}$ may be combined with each other to form a condensed benzene ring, a condensed substituted-benzene ring, trimethylene group, tetramethylene group, pentamethylene group, methylenedioxy group, ethylenedioxy group or trimethylenedioxy group;

[Chem. 7]

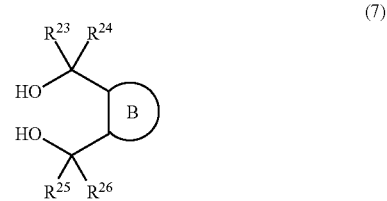
(7)

wherein $R^{23}$, $R^{24}$, $R^{25}$ and $R^{26}$ each independently represent hydrogen atom, an alkyl group having from 1 to 8 carbon atoms, an alicyclic group having from 5 to 8 carbon atoms, a perhalogenoalkyl group having from 1 to 8 carbon atoms, an alkoxy group having from 1 to 8 carbon atoms, an aralkyl group having from 7 to 12 carbon atoms, which may have a substituent, a halogen atom, an organosilyl group, an aryl group having from 6 to 15 carbon atoms, which may has a substituent, a heteroaryl group having from 2 to 15 carbon atoms, which may have a substituent, a dialkylamino group having from 2 to 8 carbon atoms, a thioalkoxy group having from 1 to 4 carbon atoms, a nitro group or a polymer chain; $R^{23}$ and $R^{24}$, and/or $R^{25}$ and $R^{26}$ may be combined with each other to form a 3- to 9-membered ring which may have a hetero element; and the ring B is a 3- to 8-membered ring which may have a hetero element; and

[Chem. 8]

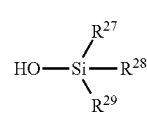
(8)

wherein $R^{27}$, $R^{28}$ and $R^{29}$ each independently represent an alkyl group having from 1 to 10 carbon atoms, an alicyclic group having from 5 to 8 carbon atoms, an aralkyl group having from 7 to 12 carbon atoms, an aryl group having from 6 to 10 carbon atoms, which may have a substituent, a heteroaryl group having from 2 to 15 carbon atoms, which may have a substituent or a polymer chain.

2. A method for producing isopulegol represented by the following formula (10), comprising selectively cyclizing citronellal represented by the following formula (9) using the organoaluminum compound according to claim 1 as a catalyst;

[Chem. 9]

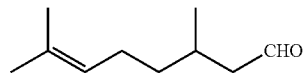
(9)

[Chem. 10]

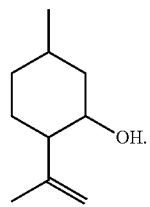
(10)

3. A method for producing optically active isopulegol represented by the following formula (12), comprising selectively cyclizing citronellal represented by the following formula (11) using the organoaluminum compound according to claim 1 as a catalyst;

[Chem. 11]

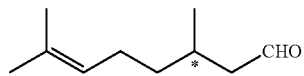
(11)

wherein * means an asymmetric carbon atom

[Chem. 12]

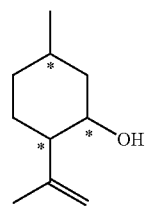
(12)

wherein * means an asymmetric carbon atom.

* * * * *